(12) United States Patent
Kudou et al.

(10) Patent No.: US 9,789,068 B2
(45) Date of Patent: *Oct. 17, 2017

(54) EASILY DOSABLE SOLID PREPARATION

(71) Applicant: Mochida Pharmaceutical Co., Ltd., Tokyo (JP)

(72) Inventors: Yumio Kudou, Tokyo (JP); Kuniomi Warabino, Tokyo (JP); Hiromitsu Ito, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,484

(22) Filed: Jan. 31, 2017

(65) Prior Publication Data

US 2017/0151178 A1    Jun. 1, 2017

Related U.S. Application Data

(63) Continuation of application No. 14/345,708, filed as application No. PCT/JP2011/072631 on Sep. 30, 2011, now Pat. No. 9,603,805.

(51) Int. Cl.
| | | |
|---|---|---|
| A61K 9/28 | (2006.01) | |
| A61K 9/00 | (2006.01) | |
| A61K 31/5383 | (2006.01) | |
| A61K 31/522 | (2006.01) | |

(52) U.S. Cl.
CPC .......... *A61K 9/2866* (2013.01); *A61K 9/0053* (2013.01); *A61K 9/282* (2013.01); *A61K 9/284* (2013.01); *A61K 9/286* (2013.01); *A61K 9/2813* (2013.01); *A61K 9/2826* (2013.01); *A61K 31/522* (2013.01); *A61K 31/5383* (2013.01)

(58) Field of Classification Search
CPC .......... A61K 9/486; A61K 9/006; A61K 9/20; A61K 9/2004; A61K 9/2054; A61K 9/2059; A61K 9/2806; A61K 9/28; A61K 9/2826; A61K 9/286; A61K 9/2893
See application file for complete search history.

(56) References Cited

U.S. PATENT DOCUMENTS

| | | | |
|---|---|---|---|
| 4,439,194 A | 3/1984 | Harwood et al. | |
| 5,536,511 A | 7/1996 | Yatka | |
| 6,261,601 B1 | 7/2001 | Talwar et al. | |
| 6,709,678 B2 | 3/2004 | Gruber | |
| 7,785,650 B2 | 8/2010 | Gulian et al. | |
| 8,123,849 B2 | 2/2012 | Rajsharad et al. | |
| 9,603,805 B2 * | 3/2017 | Kudou ................... | A61K 9/284 |
| 2001/0018070 A1 | 8/2001 | Shell et al. | |
| 2002/0068088 A1 | 6/2002 | Gruber | |
| 2003/0215585 A1 | 11/2003 | Bunick | |
| 2004/0101567 A1 | 5/2004 | Nomura | |
| 2004/0137040 A1 | 7/2004 | Nogami | |
| 2005/0208135 A1 | 9/2005 | Viswanathan et al. | |
| 2006/0068058 A1 | 3/2006 | Boghani | |
| 2006/0165801 A1 | 7/2006 | Ishii | |
| 2007/0140992 A1 | 6/2007 | Schick | |
| 2007/0141153 A1 * | 6/2007 | Nogami ................. | A61K 9/006 |
| | | | 424/472 |
| 2010/0029938 A1 | 2/2010 | Puig Torres et al. | |
| 2010/0126650 A1 | 5/2010 | Kabuto et al. | |
| 2010/0255066 A1 | 10/2010 | Sugiura et al. | |
| 2011/0027325 A1 | 2/2011 | Sugiura et al. | |
| 2012/0034276 A1 | 2/2012 | Takano et al. | |
| 2012/0082723 A1 | 4/2012 | Kudou et al. | |
| 2015/0079171 A1 * | 3/2015 | Kudou ................... | A61K 9/284 |
| | | | 424/480 |

FOREIGN PATENT DOCUMENTS

| | | |
|---|---|---|
| CN | 101438734 A | 5/2009 |
| EP | 1 323 418 A1 | 7/2003 |
| EP | 1 391 212 A1 | 2/2004 |
| EP | 1 166 777 B1 | 8/2008 |
| EP | 2324826 A1 | 5/2011 |
| JP | 11-060472 A | 3/1999 |
| JP | 2000-516222 A | 12/2000 |
| JP | 2002-275054 A | 9/2002 |
| JP | 2004-520420 A | 7/2004 |
| JP | 2005-500255 A | 1/2005 |

(Continued)

OTHER PUBLICATIONS

Ansel et al., *Pharmaceutical Dosage Forms and Drug Delivery Systems*, 1999, 7th Ed., Lippincott, Williams & Wilkins, pp. 23-141 and 164-243.

Ansel et al., *Pharmaceutical Dosage Forms and Drug Delivery Systems*, 7th Ed., 1999, Lippincott, Williams & Wilkins, 207-209.

Final Office Action dated Mar. 21, 2016, in U.S. Appl. No. 14/548,495.

Huang et al., "Mechanistic Approaches to Predicting Oral Drug Absorption," The AAPS Journal, Jun. 2009, 11(2):217-224.

Kaneda et al., "Control of Drug Release from Granules by Application of Gel Formation with Calcium Lactate, Sodium Alginate and Carbopol," Journal of Pharmaceutical Science and Technology, Japan, Mar. 5, 2002, 62:287, with English translation, 2 pages.

(Continued)

*Primary Examiner* — Micah-Paul Young
(74) *Attorney, Agent, or Firm* — Foley & Lardner LLP

(57) ABSTRACT

It has been desired to develop a coating composition, which is used for an orally-administered preparation having an improved administering property, and/or an easily administrable preparation that does not affect dissolution property. The present invention provides a coating composition comprising: a first thickener selected from the group consisting of a carboxyvinyl polymer and sodium alginate; a polyvalent metal compound; at least one type of a second thickener selected from the group consisting of xanthan gum, guar gum and sodium alginate, with the proviso that when the first thickener is sodium alginate the second thickener is not sodium alginate; and sucralose.

14 Claims, No Drawings

(56) References Cited

FOREIGN PATENT DOCUMENTS

| JP | 3883505 B2 | 2/2007 |
|---|---|---|
| JP | 2009-007310 A | 1/2009 |
| JP | 2009-500318 A | 1/2009 |
| JP | 2009-501777 A | 1/2009 |
| JP | 2009-035505 A | 2/2009 |
| JP | 2009-114113 A | 5/2009 |
| JP | 4267926 B2 | 5/2009 |
| JP | 2009-536654 A | 10/2009 |
| JP | 2010-138125 A | 6/2010 |
| WO | WO 00/06122 A1 | 2/2000 |
| WO | WO 02/069939 A2 | 9/2002 |
| WO | WO 02/072034 A2 | 9/2002 |
| WO | WO 2005/027843 A2 | 3/2005 |
| WO | WO 2007/000779 A2 | 1/2007 |
| WO | WO 2007/010400 A2 | 1/2007 |
| WO | WO 2007/133583 A2 | 11/2007 |
| WO | WO 2008/025532 A1 | 11/2007 |
| WO | WO 2008/129730 A1 | 10/2008 |
| WO | WO 2009/047802 A2 | 4/2009 |
| WO | WO 2009/119290 A1 | 10/2009 |
| WO | WO 2010/018614 A1 | 2/2010 |
| WO | WO 2010/110322 A1 | 9/2010 |

OTHER PUBLICATIONS

O'Neil et al., Eds., *The Merck Index: An Encyclopedia of Chemicals, Drugs and Biologicals*, 2006, Merck & Co., Inc., entry for "Sorbitol," 1-3 (as provided by Examiner, cited in U.S. Appl. No. 13/200,759).

Office Action dated Oct. 6, 2015, in U.S. Appl. No. 14/548,495.

Okabe et al., "Development of an easily swallowed film formulation," International Journal of Pharmaceutics, 2008, 355:62-66.

Restriction Requirement dated Jul. 9, 2015 in U.S. Appl. No. 14/458,495.

Sinko, Patrick J., *Martin's Physical Pharmacy and Pharmaceutical Sciences*, 2006, 5$^{th}$ Ed., Lippincott, Williams & Wilkins, pp. 337-354.

Thakkar et al., "Goodness-of-Fit Model-Dependent Approach for Release Kinetics of Levofloxacin Hemihydrates Floating Tablet," Dissolution Technologies, Feb. 2009, 16(1):35-39.

Tønnesen et al., "Alginate in Drug Delivery Systems," Drug Development and Industrial Pharmacy, 2002, 28(6):621-630.

\* cited by examiner

EASILY DOSABLE SOLID PREPARATION

CROSS-REFERENCE TO RELATED APPLICATIONS

This application is a Continuation of U.S. application Ser. No. 14/345,708, which is the U.S. National Stage application of PCT/JP2011/072631, filed Sep. 30, 2011.

TECHNICAL FIELD

The present invention relates to an easily administrable oral preparation having an improved administering property, and/or a coating composition used for an easily administrable preparation having an improved dissolution property.

BACKGROUND ART

At present, orally-administered preparations have a high proportion of pharmaceutical preparations. Among such orally-administered preparations, solid preparations remain predominant. Such solid preparations include many high-dose solid preparations. When such a high-dose solid preparation is prepared as a single unit tablet, it becomes large in size. When it is prepared as a powder or a granule, it becomes a bulky preparation due to low density, and thus it is difficult for children and aged people whose swallowing function is low to take such bulky preparation in many cases.

A technique of producing an orally fast-disintegrating tablet has been developed to enhance the administering property of a tablet. However, since the content of a principal agent is small with respect to the total content of the tablet, this technique is not suitable for producing a preparation containing a large amount of principal agent. In a case in which an orally fast-disintegrating tablet is grown in size, it causes a great feeling of a foreign body in the oral cavity after disintegration of the tablet. Moreover, such an orally fast-disintegrating tablet is also problematic in that it is difficult to mask the taste when the principal agent thereof has an unpleasant taste such as a bitter taste.

Furthermore, preparations such as a liquid agent or a jelly agent have also been proposed as dosage forms having a good administering property. However, even in the case of these dosage forms, when the content of a principal agent is high, it is difficult to perform taste masking, and further, stability in water has not been achieved.

An example of a high-dose preparation is an anticholesteremic agent comprising, as an active ingredient, cholestimide that is an anion exchange resin. In order to reduce the preparation in size for easy administration, a multi-unit preparation (a mini-tablet divided agent) has been developed and has been on the market. Japanese Patent No. 3883505 (Patent Literature 1) describes that, in order to improve the administering property of a multi-unit preparation (mini-tablet) of cholestimide, the drug is coated with a water-soluble polymer cellulose and is further coated with ethylcellulose, so as to prevent deterioration of the administering property due to disintegration and aggregation of the mini-tablet in the oral cavity. However, this publication does not describe a technique of improving the slipping property of the tablet to cause easy swallowing.

In recent years, a method of making it easy to swallow a solid agent, a technique of using a gelling agent that causes a favorable slipping property on the mucosa has being developed. For example, JP Patent Publication (Kohyo) No. 2000-516222 A (Patent Literature 2) describes a preparation, in which a granule, a pellet or a mini-tablet is coated with a high-viscosity gelling agent as an inner layer and is coated with a low-viscosity gelling agent as an outer layer, so as to improve cohesiveness of the preparation in the oral cavity, the masking of a bitter taste and easy swallowability. However, the disclosed method is disadvantageous in that it takes a long time to form a gel and in that the formed gel highly adheres to the mucosa.

JP Patent Publication (Kokai) No. 2002-275054 A (Patent Literature 3) describes an easily swallowable tablet, which is coated with a coating solution, in which xanthan gum is used as a gelling agent and 40 parts or more of sugar alcohol is added to 100 parts of solid components. With regard to this coating, the tablet causes no slime or stickiness when it is placed in the oral cavity, and the slipping property on the mucosa is said to be favorable. However, a single use of xanthan gum as a gelling agent forms an excessively soft gel in the oral cavity, the masking of a bitter taste is insufficient, and it is desired to further improve its slipping property on the mucosa.

Japanese Patent No. 4267926 (Patent Literature 4) discloses a gelling film preparation. The publication describes that this film preparation is a sheet-like preparation formed by sandwiching a drug layer between carboxyvinyl polymer layers crosslinked by polyvalent metal salts, and that it rapidly turns into a gel in the oral cavity. It also describes that the film preparation is rarely stuck in the throat, and that a bitter taste can be masked. However, the publication does not describe the coating of a tablet or a granule. Since the carboxyvinyl polymer used in the present technique is subjected to a production process in the form of a solution having extremely high viscosity that has been crosslinked with polyvalent metal ions, it is considered difficult for the solution to be applied by spray-coating onto a tablet or a granule (see the after-mentioned Reference Example 1). Thus, the preparation that can be produced by the present technique is a film dosage form, and it needs a special process called "application" and a special apparatus. When compared with the spray-coating of a tablet or a granule, a production cost tends to become high. Moreover, as described in the after-mentioned Reference Example 2, a coated mini-tablet produced by modifying the present technique such that the preparation can be applied by spray-coating could not achieve practically satisfactory, easy swallowability.

On the other hand, when coating is carried out using a gelling agent, there is a fear that diffusion of the drug will be suppressed by formation of a gel in the gastrointestinal tract, and a delay in dissolution will occur. JP Patent Publication (Kokai) No. 11-60472 A (1999) (Patent Literature 5) discloses that sugars are added to an easily swallowable coated tablet that has been coated with methylcellulose, so as to prevent a delay in dissolution. However, when a mini-tablet is produced from this coated tablet, cohesiveness in the oral cavity cannot be expected.

Hence, it is an important object to prevent a delay in dissolution of a drug from a preparation coated with a gelling agent.

CITATION LIST

Patent Literature

Patent Literature 1: Japanese Patent No. 3883505
Patent Literature 2: JP Patent Publication (Kohyo) No. 2000-516222 A
Patent Literature 3: JP Patent Publication (Kokai) No. 2002-275054 A
Patent Literature 4: Japanese Patent No. 4267926
Patent Literature 5: JP Patent Publication (Kokai) No. 11-60472 A (1999)

SUMMARY OF INVENTION

Problem to be Solved by the Invention

As described above, in the field of orally-administered preparations, and particularly, in the field of high-dose preparations such as large tablets, it has been desired to develop an easily producible coated preparation having the effect of masking an unpleasant taste such as a bitter taste and good swallowability. In addition, it has also been desired to develop a coated preparation with an improved dissolution property. It is an object of the present invention to provide a coated preparation having any one or more of, and preferably, all of the aforementioned properties, and a coating composition used to produce the coated preparation.

Means for Solving the Problems

Considering the above-mentioned object, the present inventors have conducted intensive studies for the purpose of improving the administering property of an oral preparation. As a result, the inventors have found that an orally-administered solid preparation, such as a tablet, is coated with a coating composition, which comprises a combination of a first thickener such as a carboxyvinyl polymer with a second thickener such as xanthan gum, and a small amount of polyvalent metal compound used as a viscosity adjuster, so that an unpleasant taste can be masked, so that the preparation can be easily swallowed because it easily slips on the mucosa, and so that the production thereof becomes easy. Moreover, the inventors have found that sucralose is added to the coating composition, so that such an unpleasant taste-masking effect can be further improved. Furthermore, the inventors have also found that hydroxypropylmethylcellulose (hereinafter also referred to as HPMC) and sugar or sugar alcohol having specific properties are added to the thickeners, so that the film of the preparation is disintegrated immediately after it has been swallowed, so as to prevent a delay in dissolution, thereby completing the present invention.

Specifically, a first aspect of the present invention relates to the following coating composition.

[1-1] A coating composition comprising:
a first thickener that is a metal-crosslinked thickener, and preferably, a first thickener selected from the group consisting of a carboxyvinyl polymer and sodium alginate;
a polyvalent metal compound; and
at least one type of a second thickener selected from the group consisting of xanthan gum, guar gum and sodium alginate, with the proviso that when the first thickener is sodium alginate the second thickener is not sodium alginate.

[1-1a] A coating composition comprising a carboxyvinyl polymer, a polyvalent metal compound and xanthan gum.

[1-2] The coating composition according to [1-1] above, wherein the first thickener is a carboxyvinyl polymer or sodium alginate that is not substantially crosslinked by polyvalent metal ions.

[1-2a] The coating composition according to [1-1a] above, wherein the carboxyvinyl polymer is not substantially crosslinked.

[1-3] The coating composition according to any one of [1-1], [1-2], [1-1a] and [1-2a] above, which further comprises sugar or sugar alcohol having a solubility at 20° C. of 30 or more.

[1-4] The coating composition according to any one of [1-1] to [1-3], [1-1a] and [1-2a] above, which further comprises HPMC.

[1-5] The coating composition according to [1-4] above, which is characterized in that the content of the first thickener is 3% to 15% by mass or 3% to 20% by mass (% by mass based on the total mass of all ingredients excluding a solvent; the same applies below), the content of the second thickener is 10% to 40% by mass, the content of the HPMC is 5% to 35% by mass, and the content of the sugar or sugar alcohol is 10% to 50% by mass.

[1-5a] The coating composition according to [1-4] above, which is characterized in that the content of the carboxyvinyl polymer is 3% to 15% by mass or 3% to 20% by mass (% by mass based on the total mass of all ingredients excluding a solvent; the same applies below), the content of the xanthan gum is 10% to 40% by mass, the content of the HPMC is 5% to 35% by mass, and the content of the sugar or sugar alcohol is 10% to 50% by mass.

[1-6] The coating composition according to any one of [1-1] to [1-5] above, which is characterized in that the content of the polyvalent metal compound is 2% to 15% by mass based on the content of the first thickener.

[1-6a] The coating composition according to any one of [1-1a], [1-2a], [1-3], [1-4] and [1-5a] above, which is characterized in that the content of the polyvalent metal compound is 2% to 15% by mass based on the content of the carboxyvinyl polymer.

[1-7] The coating composition according to any one of [1-1] to [1-6], [1-1a], [1-2a], [1-5a] and [1-6a] above, which is characterized in that it comprises alcohol as a solvent.

[1-8] The coating composition according to any one of [1-1] to [1-7], [1-1a], [1-2a], [1-5a] and [1-6a] above, which further comprises sucralose.

[1-9] The coating composition according to [1-8] above, which is characterized in that the content of the first thickener is 3% to 20% by mass (% by mass based on the total mass of all ingredients excluding a solvent; the same applies below), the content of the second thickener is 10% to 40% by mass, the content of the sucralose is 0.01% to 5% by mass, the content of the HPMC is 5% to 35% by mass, and the content of the sugar or sugar alcohol is 10% to 50% by mass.

[1-9a] The coating composition according to [1-8] above, which is characterized in that the content of the carboxyvinyl polymer is 3% to 20% by mass (% by mass based on the total mass of all ingredients excluding a solvent; the same applies below), the content of the xanthan gum is 10% to 40% by mass, the content of the sucralose is 0.01% to 5% by mass, the content of the HPMC is 5% to 35% by mass, and the content of the sugar or sugar alcohol is 10% to 50% by mass.

An oral composition coated with the coating composition of the first aspect of the present invention has a favorable slipping property and favorable swallowability without adhesion to the mucosa. Otherwise, a sufficient effect of masking an unpleasant taste can be obtained. Preferably, the present oral composition has both of the two above effects. The coating composition in another preferred aspect has an improved drug-dissolution property. The coating composition in a further preferred aspect can be easily applied by spray-coating to a drug core, and it can also be easily dried.

In addition, a second aspect of the present invention relates to the following oral composition.

[2-1] An oral composition having:
a drug core containing an active ingredient; and
over the drug core,
a coating comprising
 a first thickener that is a metal-crosslinked thickener, and preferably, a first thickener selected from the group consisting of a carboxyvinyl polymer and sodium alginate,
 a polyvalent metal compound, and
 at least one type of a second thickener selected from the group consisting of xanthan gum, guar gum and sodium alginate, with the proviso that when the first thickener is sodium alginate the second thickener is not sodium alginate.

[2-1a] An oral composition having a drug core containing an active ingredient, and over the drug core, a coating comprising a carboxyvinyl polymer, a polyvalent metal compound and xanthan gum.

[2-2] The oral composition according to [2-1] above, wherein the first thickener is a carboxyvinyl polymer or sodium alginate that is not substantially crosslinked by polyvalent metal ions.

[2-2a] The oral composition according to [2-1a] above, wherein the carboxyvinyl polymer is not substantially crosslinked.

[2-3] The oral composition according to any one of [2-1], [2-2], [2-1a] and [2-2a] above, wherein the coating further comprises sugar or sugar alcohol having a solubility at 20° C. of 30 or more.

[2-4] The oral composition according to any one of [2-1] to [2-3], [2-1a] and [2-2a] above, wherein the coating further comprises HPMC.

[2-5] The oral composition according to [2-4] above, which is characterized in that the content of the first thickener is 3% to 15% by mass or 3% to 20% by mass (% by mass based on the total mass of all ingredients in the coating; the same applies below), the content of the second thickener is 10% to 40% by mass, the content of the HPMC is 5% to 35% by mass, and the content of the sugar or sugar alcohol is 10% to 50% by mass.

[2-5a] The oral composition according to [2-4] above, which is characterized in that the content of the carboxyvinyl polymer is 3% to 15% by mass or 3% to 20% by mass (% by mass based on the total mass of all ingredients in the coating; the same applies below), the content of the xanthan gum is 10% to 40% by mass, the content of the HPMC is 5% to 35% by mass, and the content of the sugar or sugar alcohol is 10% to 50% by mass.

[2-6] The oral composition according to any one of [2-1] to [2-5] above, which is characterized in that the content of the polyvalent metal compound is 2% to 15% by mass based on the content of the first thickener.

[2-6a] The oral composition according to any one of [2-1a], [2-2a], [2-3], [2-4] and [2-5a] above, which is characterized in that the content of the polyvalent metal compound is 2% to 15% by mass based on the content of the carboxyvinyl polymer.

[2-7] The oral composition according to any one of [2-1] to [2-6], [2-1a], [2-2a], [2-5a] and [2-6a] above, which is characterized in that the drug core is a tablet core containing an active ingredient.

[2-8] The oral composition according to any one of [2-1] to [2-7] above, wherein the second thickener is at least one type of thickener selected from the group consisting of xanthan gum, guar gum, and sodium alginate that is not substantially crosslinked by polyvalent metal ions.

[2-9] The oral composition according to any one of [2-1] to [2-8], [2-1a], [2-2a], [2-5a] and [2-6a] above, which further has a seal coating between the drug core and the coating.

[2-10] The oral composition according to any one of [2-1] to [2-9], [2-1a], [2-2a], [2-5a] and [2-6a] above, wherein the coating further comprises sucralose.

[2-11] The oral composition according to [2-10] above, which is characterized in that the content of the first thickener is 3% to 20% by mass (% by mass based on the total mass of all ingredients in the coating; the same applies below), the content of the second thickener is 10% to 40% by mass, the content of the sucralose is 0.01% to 5% by mass, the content of the HPMC is 5% to 35% by mass, and the content of the sugar or sugar alcohol is 10% to 50% by mass.

[2-11a] The oral composition according to [2-10] above, which is characterized in that the content of the carboxyvinyl polymer is 3% to 20% by mass (% by mass based on the total mass of all ingredients in the coating; the same applies below), the content of the xanthan gum is 10% to 40% by mass, the content of the sucralose is 0.01% to 5% by mass, the content of the HPMC is 5% to 35% by mass, and the content of the sugar or sugar alcohol is 10% to 50% by mass.

[2-12] The oral composition according to any one of [2-9] to [2-11] and [2-11a] above, which further has a middle coating between the seal coating and the coating.

The oral composition of the second aspect of the present invention has a favorable slipping property and favorable swallowability without adhesion to the mucosa. Otherwise, an effect of masking an unpleasant taste can be obtained. Preferably, the present oral composition has both of the two above effects. The oral composition in another preferred aspect has an improved drug-dissolution property.

Moreover, a third aspect of the present invention relates to the following oral composition.

[3-1] An oral composition, which is obtained by spray-coating a drug core containing an active ingredient with a liquid that has been prepared by dispersing a first thickener that is a metal-crosslinked thickener, and preferably, a first thickener selected from the group consisting of a carboxyvinyl polymer and sodium alginate, and at least one type of a second thickener selected from the group consisting of xanthan gum, guar gum and sodium alginate, with the proviso that when the first thickener is sodium alginate the second thickener is not sodium alginate, into an alcohol solution in which a polyvalent metal compound has been dissolved.

[3-1a] An oral composition, which is obtained by spray-coating a drug core containing an active ingredient with a liquid that has been prepared by dispersing a carboxyvinyl polymer and xanthan gum into an alcohol solution in which a polyvalent metal compound has been dissolved.

[3-2] The oral composition according to [3-1] above, wherein the first thickener is a carboxyvinyl polymer or sodium alginate that is not substantially crosslinked by polyvalent metal ions.

[3-2a] The oral composition according to [3-1a] above, wherein the carboxyvinyl polymer is not substantially crosslinked.

[3-3] The oral composition according to any one of [3-1], [3-2], [3-1a] and [3-2a] above, which is characterized in that sugar or sugar alcohol having a solubility at 20° C. of 30 or more is further dispersed into the liquid used for the spray-coating.

[3-4] The oral composition according to any one of [3-1] to [3-3], [3-1a] and [3-2a] above, wherein the liquid used for the spray-coating further comprises HPMC.

[3-5] The oral composition according to [3-4] above, which is characterized in that, in the liquid used for the spray-coating, the content of the first thickener is 3% to 15% by mass or 3% to 20% by mass (% by mass based on the total mass of all ingredients excluding a solvent; the same applies below), the content of the second thickener is 10% to 40% by mass, the content of the HPMC is 5% to 35% by mass, and the content of the sugar or sugar alcohol is 10% to 50% by mass.

[3-5a] The oral composition according to [3-4] above, which is characterized in that, in the liquid used for the spray-coating, the content of the carboxyvinyl polymer is 3% to 15% by mass or 3% to 20% by mass (% by mass based on the total mass of all ingredients excluding a solvent; the same applies below), the content of the xanthan gum is 10% to 40% by mass, the content of the HPMC is 5% to 35% by mass, and the content of the sugar or sugar alcohol is 10% to 50% by mass.

[3-6] The oral composition according to any one of [3-1] to [3-5] above, which is characterized in that the content of the polyvalent metal compound is 2% to 15% by mass based on the content of the first thickener.

[3-6a] The oral composition according to any one of [3-1a], [3-2a], [3-3], [3-4] and [3-5a] above, which is characterized in that the content of the polyvalent metal compound is 2% to 15% by mass based on the content of the carboxyvinyl polymer.

[3-7] The oral composition according to any one of [3-1] to [3-6], [3-1a], [3-2a], [3-5a] and [3-6a] above, which is characterized in that the drug core is a tablet core containing an active ingredient.

[3-8] The oral composition according to any one of [3-1] to [3-7] above, wherein the second thickener is at least one type of thickener selected from the group consisting of xanthan gum, guar gum, and sodium alginate that is not substantially crosslinked by polyvalent metal ions.

[3-9] The oral composition according to any one of [3-1] to [3-8], [3-1a], [3-2a], [3-5a] and [3-6a] above, wherein the drug core, to which the spray coating is performed, is a seal-coated drug core having a seal coating.

[3-10] The oral composition according to any one of [3-1] to [3-9], [3-1a], [3-2a], [3-5a] and [3-6a] above, wherein the liquid used for the spray-coating further comprises sucralose.

[3-11] The oral composition according to [3-10] above, which is characterized in that, in the liquid used for the spray-coating, the content of the first thickener is 3% to 20% by mass (% by mass based on the total mass of all ingredients excluding a solvent; the same applies below), the content of the second thickener is 10% to 40% by mass, the content of the sucralose is 0.01% to 5% by mass, the content of the HPMC is 5% to 35% by mass, and the content of the sugar or sugar alcohol is 10% to 50% by mass.

[3-11a] The oral composition according to [3-10] above, which is characterized in that, in the liquid used for the spray-coating, the content of the carboxyvinyl polymer is 3% to 20% by mass (% by mass based on the total mass of all ingredients excluding a solvent; the same applies below), the content of the xanthan gum is 10% to 40% by mass, the content of the sucralose is 0.01% to 5% by mass, the content of the HPMC is 5% to 35% by mass, and the content of the sugar or sugar alcohol is 10% to 50% by mass.

[3-12] The oral composition according to any one of [3-9] to [3-11] and [3-11a], wherein the seal-coated drug core further has a middle coating over the seal coating.

The oral composition of the third aspect of the present invention has a favorable slipping property and favorable swallowability without adhesion to the mucosa. Otherwise, a sufficient effect of masking an unpleasant taste can be obtained. Preferably, the present oral composition has both of the two above effects. The oral composition in another preferred aspect has an improved drug-dissolution property.

Furthermore, a fourth aspect of the present invention relates to the following method for producing an oral composition.

[4-1] A method for producing an oral composition, which is characterized in that it comprises spray-coating a drug core containing an active ingredient with a liquid that has been prepared by dispersing a first thickener that is a metal-crosslinked thickener, and preferably, a first thickener selected from the group consisting of a carboxyvinyl polymer and sodium alginate, and at least one type of a second thickener selected from the group consisting of xanthan gum, guar gum and sodium alginate, with the proviso that when the first thickener is sodium alginate the second thickener is not sodium alginate, into an alcohol solution in which a polyvalent metal compound has been dissolved.

[4-1a] A method for producing an oral composition, which is characterized in that it comprises spray-coating a drug core containing an active ingredient with a liquid that has been prepared by dispersing a carboxyvinyl polymer and xanthan gum into an alcohol solution in which a polyvalent metal compound has been dissolved.

[4-2] The method for producing an oral composition according to [4-1] above, wherein the first thickener is a carboxyvinyl polymer or sodium alginate that is not substantially crosslinked by polyvalent metal ions.

[4-2a] The method for producing an oral composition according to [4-1a] above, wherein the carboxyvinyl polymer is not substantially crosslinked.

[4-3] The method for producing an oral composition according to any one of [4-1], [4-2], [4-1a] and [4-2a] above, which is characterized in that sugar or sugar alcohol having a solubility at 20° C. of 30 or more is further dispersed into the liquid used for the spray-coating.

[4-4] The method for producing an oral composition according to any one of [4-1] to [4-3], [4-1a] and [4-2a] above, wherein the liquid used for the spray-coating further comprises HPMC.

[4-5] The method for producing an oral composition according to [4-4] above, which is characterized in that, in the liquid used for the spray-coating, the content of the first thickener is 3% to 15% by mass or 3% to 20% by mass (% by mass based on the total mass of all ingredients excluding a solvent; the same applies below), the content of the second thickener is 10% to 40% by mass, the content of the HPMC is 5% to 35% by mass, and the content of the sugar or sugar alcohol is 10% to 50% by mass.

[4-5a] The method for producing an oral composition according to [4-4] above, which is characterized in that, in the liquid used for the spray-coating, the content of the carboxyvinyl polymer is 3% to 15% by mass or 3% to 20% by mass (% by mass based on the total mass of all ingredients excluding a solvent; the same applies below), the content of the xanthan gum is 10% to 40% by mass, the content of the HPMC is 5% to 35% by mass, and the content of the sugar or sugar alcohol is 10% to 50% by mass.

[4-6] The method for producing an oral composition according to any one of [4-1] to [4-5] above, which is characterized in that the content of the polyvalent metal compound is 2% to 15% by mass based on the content of the first thickener.

[4-6a] The method for producing an oral composition according to any one of [4-1a], [4-2a], [4-3], [4-4] and [4-5a] above, which is characterized in that the content of the polyvalent metal compound is 2% to 15% by mass based on the content of the carboxyvinyl polymer.

[4-7] The method for producing an oral composition according to any one of [4-1] to [4-6], [4-1a], [4-2a], [4-5a] and [4-6a] above, which is characterized in that the drug core is a tablet core containing an active ingredient.

[4-8] The method for producing an oral composition according to any one of [4-1] to [4-7] above, wherein the second thickener is at least one type of thickener selected from the group consisting of xanthan gum, guar gum, and sodium alginate that is not substantially crosslinked by polyvalent metal ions.

[4-9] The method for producing an oral composition according to any one of [4-1] to [4-8], [4-1a], [4-2a], [4-5a] and [4-6a] above, wherein the drug core, to which the spray coating is performed, is a seal-coated drug core having a seal coating.

[4-10] The method for producing an oral composition according to any one of [4-1] to [4-9], [4-1a], [4-2a], [4-5a] and [4-6a] above, wherein the liquid used for the spray-coating further comprises sucralose.

[4-11] The method for producing an oral composition according to [4-10] above, which is characterized in that, in the liquid used for the spray-coating, the content of the first thickener is 3% to 20% by mass (% by mass based on the total mass of all ingredients excluding a solvent; the same applies below), the content of the second thickener is 10% to 40% by mass, the content of the sucralose is 0.01% to 5% by mass, the content of the HPMC is 5% to 35% by mass, and the content of the sugar or sugar alcohol is 10% to 50% by mass.

[4-11a] The method for producing an oral composition according to [4-10] above, which is characterized in that, in the liquid used for the spray-coating, the content of the carboxyvinyl polymer is 3% to 20% by mass (% by mass based on the total mass of all ingredients excluding a solvent; the same applies below), the content of the xanthan gum is 10% to 40% by mass, the content of the sucralose is 0.01% to 5% by mass, the content of the HPMC is 5% to 35% by mass, and the content of the sugar or sugar alcohol is 10% to 50% by mass.

[4-12] The method for producing an oral composition according to any one of [4-9] to [4-11] and [4-11a], wherein the seal-coated drug core further has a middle coating over the seal coating.

The method for producing an oral composition of the fourth aspect of the present invention can be easily applied by spray-coating to a drug core and it can also be easily dried. In addition, the oral composition obtained by the present production method has a favorable slipping property and favorable swallowability without adhesion to the mucosa. Otherwise, a sufficient effect of masking an unpleasant taste can be obtained. Preferably, the present oral composition has both of the two above effects. The oral composition obtained by the production method in another preferred aspect has an improved drug-dissolution property.

Furthermore, a fifth aspect of the present invention relates to the following coating composition.

[5-1] A coating composition comprising a thickener that turns into a gel when it is allowed to come into contact with water, sugar or sugar alcohol having a solubility at 20° C. of 30 or more, and HPMC.

[5-2] The coating composition according to [5-1] above, wherein the thickener is at least one type selected from the group consisting of xanthan gum, guar gum and sodium alginate.

[5-2a] The coating composition according to [5-1] above, wherein the thickener comprises xanthan gum.

[5-3] The coating composition according to [5-1] above, wherein the thickener is selected from the group consisting of a carboxyvinyl polymer and sodium alginate.

[5-3a] The coating composition according to [5-1] above, wherein the thickener comprises a carboxyvinyl polymer.

[5-4] The coating composition according to [5-1] above, wherein the thickener comprises one type selected from the group consisting of a carboxyvinyl polymer and sodium alginate, and at least one type selected from the group consisting of xanthan gum, guar gum and sodium alginate, with the proviso that a combination of the same substances is excluded.

[5-4a] The coating composition according to [5-1] above, wherein the thickener comprises a carboxyvinyl polymer and xanthan gum.

[5-5] The coating composition according to [5-3], [5-4], [5-3a] or [5-4a] above, which further comprises a polyvalent metal compound.

[5-6] The coating composition according to any one of [5-1] to [5-5] and [5-2a] to [5-4a] above, which is characterized in that the mixing ratio between the HPMC and the sugar or sugar alcohol is 1:1 to 1:4.

[5-7] The coating composition according to any one of [5-4] to [5-6] above, which is characterized in that the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 15% by mass or 3% to 20% by mass, and the content of at least one type selected from the group consisting of xanthan gum, guar gum and sodium alginate is 10% to 40% by mass.

[5-7a] The coating composition according to any one of [5-4a], [5-5] and [5-6] above, which is characterized in that the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 15% by mass or 3% to 20% by mass, and the content of the xanthan gum is 10% to 40% by mass.

[5-8] The coating composition according to any one of [5-1] to [5-7], [5-2a] to [5-4a], and [5-7a] above, which comprises alcohol as a solvent.

[5-9] The coating composition according to any one of [5-1] to [5-8], [5-2a] to [5-4a], and [5-7a] above, wherein the sugar or sugar alcohol is selected from the group consisting of erythritol, maltitol and trehalose.

[5-10] The coating composition according to [5-9] above, wherein the sugar or sugar alcohol is erythritol.

[5-11] The coating composition according to any one of [5-1] to [5-10], [5-2a] to [5-4a], and [5-7a] above, which further comprises sucralose.

[5-12] The coating composition according to [5-11] above, which is characterized in that the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 20% by mass, the content of at least one type selected from the group consisting of xanthan gum, guar gum and sodium alginate is 10% to 40% by mass, and the content of the sucralose is 0.01% to 5% by mass.

[5-12a] The coating composition according to [5-11] above, which is characterized in that the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 20% by mass, the content of the xanthan gum is 10% to 40% by mass, and the content of the sucralose is 0.01% to 5% by mass.

The oral composition coated with the coating composition of the fifth aspect of the present invention exhibits a drug-dissolution property that is almost equivalent to that of an uncoated oral composition. Moreover, the coating composition in a preferred aspect has a favorable slipping property and favorable swallowability without adhesion to the mucosa. Otherwise, an effect of masking an unpleasant taste can be obtained. Preferably, the present coating composition has both of the two above effects. The coating composition in another preferred aspect can be easily applied by spray-coating to a drug core, and it can also be easily dried.

Further, a sixth aspect of the present invention relates to the following oral composition.

[6-1] An oral composition having: a drug core containing an active ingredient; and a coating comprising a thickener that turns into a gel when it is allowed to come into contact with water, sugar or sugar alcohol having a solubility at 20° C. of 30 or more, and HPMC.

[6-2] The oral composition according to [6-1] above, wherein the thickener is at least one type selected from the group consisting of xanthan gum, guar gum and sodium alginate.

[6-2a] The oral composition according to [6-1] above, wherein the thickener comprises xanthan gum.

[6-3] The oral composition according to [6-1] above, wherein the thickener is selected from the group consisting of a carboxyvinyl polymer and sodium alginate.

[6-3a] The oral composition according to [6-1] above, wherein the thickener comprises a carboxyvinyl polymer.

[6-4] The oral composition according to [6-1] above, wherein the thickener comprises one type selected from the group consisting of a carboxyvinyl polymer and sodium alginate, and at least one type selected from the group consisting of xanthan gum, guar gum and sodium alginate with the proviso that a combination of the same substances is excluded.

[6-4a] The oral composition according to [6-1] above, wherein the thickener comprises a carboxyvinyl polymer and xanthan gum.

[6-5] The oral composition according to any one of [6-3], [6-4], [6-3a] and [6-4a] above, wherein the coating further comprises a polyvalent metal compound.

[6-6] The oral composition according to any one of [6-1] to [6-5] and [6-2a] to [6-4a] above, which is characterized in that the mixing ratio between the HPMC and the sugar or sugar alcohol is 1:1 to 1:4.

[6-7] The oral composition according to any one of [6-4] to [6-6] above, which is characterized in that the content of the HPMC is 5% to 35% by mass (% by mass based on the total mass of all ingredients in the coating; the same applies below), the content of the sugar or sugar alcohol is 10% to 50% by mass, the content of one type selected from the group consisting of a carboxyvinyl polymer and sodium alginate is 3% to 15% by mass or 3% to 20% by mass, and the content of at least one type selected from the group consisting of xanthan gum, guar gum and sodium alginate is 10% to 40% by mass.

[6-7a] The oral composition according to any one of [6-4a], [6-5] and [6-6] above, which is characterized in that the content of the HPMC is 5% to 35% by mass (% by mass based on the total mass of all ingredients in the coating; the same applies below), the content of the sugar or sugar alcohol is 10% to 50% by mass, the content of the carboxyvinyl polymer is 3% to 15% by mass or 3% to 20% by mass, and the content of the xanthan gum is 10% to 40% by mass.

[6-8] The oral composition according to any one of [6-1] to [6-7], [6-2a] to [6-4a], and [6-7a] above, wherein the drug core is a seal-coated drug core having a seal coating.

[6-9] The oral composition according to any one of [6-1] to [6-8], [6-2a] to [6-4a], and [6-7a] above, wherein the sugar or sugar alcohol is selected from the group consisting of erythritol, maltitol and trehalose.

[6-10] The oral composition according to [6-9] above, wherein the sugar or sugar alcohol is erythritol.

[6-11] The oral composition according to any one of [6-1] to [6-10], [6-2a] to [6-4a], and [6-7a] above, wherein the coating further comprises sucralose.

[6-12] The oral composition according to [6-11] above, which is characterized in that the content of the HPMC is 5% to 35% by mass (% by mass based on the total mass of all ingredients in the coating; the same applies below), the content of the sugar or sugar alcohol is 10% to 50% by mass, the content of one type selected from the group consisting of a carboxyvinyl polymer and sodium alginate is 3% to 20% by mass, the content of at least one type selected from the group consisting of xanthan gum, guar gum and sodium alginate is 10% to 40% by mass, and the content of the sucralose is 0.01% to 5% by mass.

[6-12a] The oral composition according to [6-11] above, which is characterized in that the content of the HPMC is 5% to 35% by mass (% by mass based on the total mass of all ingredients in the coating; the same applies below), the content of the sugar or sugar alcohol is 10% to 50% by mass, the content of the carboxyvinyl polymer is 3% to 20% by mass, the content of the xanthan gum is 10% to 40% by mass, and the content of the sucralose is 0.01% to 5% by mass.

[6-13] The oral composition according to any one of [6-8] to [6-12] and [6-12a] above, wherein the seal-coated drug core further has a middle coating over the seal coating.

The oral composition of the sixth aspect of the present invention exhibits a drug-dissolution property that is almost equivalent to that of an uncoated oral composition, although it is coated with a thickener. Moreover, the oral composition in a preferred aspect has a favorable slipping property and favorable swallowability without adhesion to the mucosa. Otherwise, a sufficient effect of masking an unpleasant taste can be obtained. Preferably, the present oral composition has both of the two above effects.

Further, a seventh aspect of the present invention relates to the following oral composition.

[7-1] An oral composition, which is obtained by spray-coating a drug core containing an active ingredient with a liquid that has been prepared by dispersing a thickener that turns into a gel when it is allowed to come into contact with water, sugar or sugar alcohol having a solubility at 20° C. of 30 or more, and HPMC, into an alcohol solution.

[7-2] The oral composition according to [7-1] above, wherein the thickener is at least one type selected from the group consisting of xanthan gum, guar gum and sodium alginate.

[7-2a] The oral composition according to [7-1] above, wherein the thickener comprises xanthan gum.

[7-3] The oral composition according to [7-1] above, wherein the thickener is selected from the group consisting of a carboxyvinyl polymer and sodium alginate.

[7-3a] The oral composition according to [7-1] above, wherein the thickener comprises a carboxyvinyl polymer.

[7-4] The oral composition according to [7-1] above, wherein the thickener comprises one type selected from the group consisting of a carboxyvinyl polymer and sodium alginate, and at least one type selected from the group consisting of xanthan gum, guar gum and sodium alginate with the proviso that a combination of the same substances is excluded.

[7-4a] The oral composition according to [7-1] above, wherein the thickener comprises a carboxyvinyl polymer and xanthan gum.

[7-5] The oral composition according to [7-3], [7-4], [7-3a] or [7-4a] above, wherein the liquid used for the spray-coating further comprises a polyvalent metal compound.

[7-6] The oral composition according to any one of [7-1] to [7-5] and [7-2a] to [7-4a] above, which is characterized in that the mixing ratio between the HPMC and the sugar or sugar alcohol in the liquid used for the spray-coating is 1:1 to 1:4.

[7-7] The oral composition according to any one of [7-4] to [7-6] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 15% by mass or 3% to 20% by mass, and the content of at least one type selected from the group consisting of xanthan gum, guar gum and sodium alginate is 10% to 40% by mass.

[7-7a] The oral composition according to any one of [7-4a], [7-5] and [7-6] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 15% by mass or 3% to 20% by mass, and the content of the xanthan gum is 10% to 40% by mass.

[7-8] The oral composition according to any one of [7-1] to [7-7], [7-2a] to [7-4a], and [7-7a] above, wherein the drug core to be spray-coated is a seal-coated drug core having a seal coating.

[7-9] The oral composition according to any one of [7-1] to [7-8], [7-2a] to [7-4a], and [7-7a] above, wherein the sugar or sugar alcohol is selected from the group consisting of erythritol, maltitol and trehalose.

[7-10] The oral composition according to [7-9] above, wherein the sugar or sugar alcohol is erythritol.

[7-11] The oral composition according to any one of [7-1] to [7-10], [7-2a] to [7-4a], and [7-7a] above, wherein the liquid used for the spray-coating further comprises sucralose.

[7-12] The oral composition according to [7-11] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 20% by mass, the content of at least one type selected from the group consisting of xanthan gum, guar gum and sodium alginate is 10% to 40% by mass, and the content of the sucralose is 0.01% to 5% by mass.

[7-12a] The oral composition according to [7-11] above, which is characterized in that, in the liquid used for the spray-coating, the content of the HPMC is 5% to 35% by (% by mass based on the total mass of all ingredients excluding a solvent; the same applies below), the content of the sugar or sugar alcohol is 10% to 50% by mass, the content of the carboxyvinyl polymer is 3% to 20% by mass, the content of the xanthan gum is 10% to 40% by mass, and the content of the sucralose is 0.01% to 5% by mass.

[7-13] The oral composition according to any one of [7-8] to [7-12] and [7-12a] above, wherein the seal-coated drug core further has a middle coating over the seal coating.

The oral composition of the seventh aspect of the present invention is obtained by spray-coating a drug core with an alcohol solution and then drying it. Thus, it is easy to produce the present oral composition. Moreover, the oral composition of the seventh aspect of the present invention exhibits a drug-dissolution property that is almost equivalent to that of an uncoated oral composition, although it is coated with a thickener. Furthermore, the oral composition in a preferred aspect has a favorable slipping property and favorable swallowability without adhesion to the mucosa. Otherwise, a sufficient effect of masking an unpleasant taste can be obtained. Preferably, the present oral composition has both of the two above effects.

Still further, an eighth aspect of the present invention relates to the following method for producing an oral composition.

[8-1] A method for producing an oral composition, which is characterized in that it comprises spray-coating a drug core containing an active ingredient with a liquid that has been prepared by dispersing a thickener that turns into a gel when it is allowed to come into contact with water, sugar or sugar alcohol having a solubility at 20° C. of 30 or more, and HPMC, into an alcohol solution in which a polyvalent metal compound has been dissolved.

[8-2] The method for producing an oral composition according to [8-1] above, wherein the thickener is at least one type selected from the group consisting of xanthan gum, guar gum and sodium alginate.

[8-2a] The method for producing an oral composition according to [8-1] above, wherein the thickener comprises xanthan gum.

[8-3] The method for producing an oral composition according to [8-1] above, wherein the thickener is selected from the group consisting of a carboxyvinyl polymer and sodium alginate.

[8-3a] The method for producing an oral composition according to [8-1] above, wherein the thickener comprises a carboxyvinyl polymer.

[8-4] The method for producing an oral composition according to [8-1] above, wherein the thickener comprises one type selected from the group consisting of a carboxyvinyl polymer and sodium alginate, and at least one type selected from the group consisting of xanthan gum, guar gum and sodium alginate, with the proviso that a combination of the same substances is excluded.

[8-4a] The method for producing an oral composition according to [8-1] above, wherein the thickener comprises a carboxyvinyl polymer and xanthan gum.

[8-5] The method for producing an oral composition according to any one of [8-1] to [8-4] and [8-2a] to [8-4a] above, which is characterized in that the mixing ratio between the HPMC and the sugar or sugar alcohol in the liquid used for the spray-coating is 1:1 to 1:4.

[8-6] The method for producing an oral composition according to [8-4] or [8-5] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of one type selected from the group consisting of a carboxyvinyl polymer and sodium alginate is 3% to 15% by mass or 3% to 20% by mass, and the content of at least one type selected from the group consisting of xanthan gum, guar gum and sodium alginate is 10% to 40% by mass.

[8-6a] The method for producing an oral composition according to [8-4a] or [8-5] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 15% by mass or 3% to 20% by mass, and the content of the xanthan gum is 10% to 40% by mass.

[8-7] The method for producing an oral composition according to any one of [8-1] to [8-6], [8-2a] to [8-4a], and [8-6a] above, which is characterized in that the drug core is a tablet core containing an active ingredient.

[8-8] The method for producing an oral composition according to any one of [8-1] to [8-7], [8-2a] to [8-4a], and [8-6a] above, wherein the drug core to be spray-coated is a seal-coated drug core having a seal coating.

[8-9] The method for producing an oral composition according to any one of [8-1] to [8-8], [8-2a] to [8-4a], and [8-6a] above, wherein the sugar or sugar alcohol is selected from the group consisting of erythritol, maltitol and trehalose.

[8-10] The method for producing an oral composition according to [8-9] above, wherein the sugar or sugar alcohol is erythritol.

[8-11] The method for producing an oral composition according to any one of [8-1] to [8-10], [8-2a] to [8-4a], and [8-6a] above, wherein the liquid used for the spray-coating further comprises sucralose.

[8-12] The method for producing an oral composition according to [8-11] above, which is characterized in that, in the liquid used for the spray-coating, the content of the HPMC is 5% to 35% by mass (% by mass based on the total mass of all ingredients excluding a solvent; the same applies below), the content of the sugar or sugar alcohol is 10% to 50% by mass, the content of the carboxyvinyl polymer is 3% to 20% by mass, the content of at least one type selected from the group consisting of xanthan gum, guar gum and sodium alginate is 10% to 40% by mass, and the content of the sucralose is 0.01% to 5% by mass.

[8-12a] The method for producing an oral composition according to [8-11] above, which is characterized in that, in the liquid used for the spray-coating, the content of the HPMC is 5% to 35% by (% by mass based on the total mass of all ingredients excluding a solvent; the same applies below), the content of the sugar or sugar alcohol is 10% to 50% by mass, the content of the carboxyvinyl polymer is 3% to 20% by mass, the content of the xanthan gum is 10% to 40% by mass, and the content of the sucralose is 0.01% to 5% by mass.

[8-13] The method for producing an oral composition according to any one of [8-8] to [8-12] and [8-12a] above, wherein the seal-coated drug core further has a middle coating over the seal coating.

The method for producing an oral composition of the eighth aspect of the present invention can be easily applied by spray-coating to a drug core and it can also be easily dried. In addition, the oral composition obtained by the present production method exhibits a drug-dissolution property that is almost equivalent to that of an uncoated oral composition, although it is coated with a thickener. Moreover, the coating composition obtained by the production method in a preferred aspect has a favorable slipping property and favorable swallowability without adhesion to the mucosa. Otherwise, a sufficient effect of masking an unpleasant taste can be obtained. Preferably, the coating composition has both of the two above effects.

Still further, a ninth aspect of the present invention relates to the following oral composition.

[9-1] An oral composition having:
 a drug core containing an active ingredient; and
 over the drug core,
 a coating comprising
 a gelatinous substance selected from the group consisting of a carboxyvinyl polymer and sodium alginate, which are crosslinked by polyvalent metal ions when water is present, and
 at least one type of a thickener selected from the group consisting of xanthan gum and guar gum.

[9-2] The oral composition according to [9-1] above, wherein the coating further comprises sugar or sugar alcohol having a solubility at 20° C. of 30 or more.

[9-3] The oral composition according to [9-1] or [9-2] above, wherein the coating further comprises HPMC.

[9-4] The oral composition according to [9-3] above, which is characterized in that the content of the gelatinous substance is 3% to 15% by mass or 3% to 20% by mass (% by mass based on the total mass of all ingredients in the coating; the same applies below), the content of the thickener is 10% to 40% by mass, the content of the HPMC is 5% to 35% by mass, and the content of the sugar or sugar alcohol is 10% to 50% by mass.

[9-5] The oral composition according to any one of [9-1] to [9-4] above, wherein the coating further comprises sucralose.

[9-6] The oral composition according to [9-5] above, which is characterized in that the content of the gelatinous substance is 3% to 20% by mass (% by mass based on the total mass of all ingredients in the coating; the same applies below), the content of the thickener is 10% to 40% by mass, the content of the HPMC is 5% to 35% by mass, the content of the sugar or sugar alcohol is 10% to 50% by mass, and the content of the sucralose is 0.01% to 5% by mass.

[9-7] The oral composition according to any one of [9-1] to [9-6] above, which further has a seal coating between the drug core and the coating.

[9-8] The oral composition according to [9-7] above, which further has a middle coating between the seal coating and the coating.

The oral composition of the ninth aspect of the present invention is equivalent to the oral composition of the second aspect of the present invention, which is generated by water contents present in the oral cavity, such as saliva. That is to say, the oral composition of the ninth aspect of the present invention has a favorable slipping property and favorable swallowability without adhesion to the mucosa. Otherwise, an effect of masking an unpleasant taste can be obtained.

Preferably, the present oral composition has both of the two above effects. The oral composition in a further preferred aspect has an improved drug-dissolution property.

Still further, a tenth aspect of the present invention relates to the following oral composition.

[10-1] An oral composition having:
a tablet core (preferably a mini-tablet) comprising levofloxacin hydrate as an active ingredient, and crystalline cellulose, sodium carboxymethyl starch, pregelatinized starch (e.g. SWELSTAR WB-1 (trade name)), and sodium stearyl fumarate;
over the tablet core,
a seal coating comprising HPMC (e.g. TC-5R (trade name)) and macrogol 6000 (trade name); and
over the seal coating,
a coating comprising a carboxyvinyl polymer (e.g. Carbopol 974P (trade name)), calcium chloride, xanthan gum, sucralose, HPMC (e.g. TC-5E (trade name)), erythritol, and HPC (e.g. HPC-L (trade name)).

[10-2] The oral composition according to [10-1] above, wherein
in the tablet core, the content of the levofloxacin hydrate is 69.7% by mass (% by mass based on the total mass of all ingredients excluding a solvent in the tablet core; the same applies below), the content of the crystalline cellulose is 6.2% by mass, the content of the sodium carboxymethyl starch is 17.7% by mass, the content of the pregelatinized starch is 2.7% by mass, and the content of the sodium stearyl fumarate is 3.7% by mass,
in the seal coating, the content of the HPMC is 95.2% by mass (% by mass based on the total mass of all ingredients excluding a solvent in the seal coating; the same applies below), and the content of the macrogol 6000 (trade name) is 4.8% by mass, and
in the coating, the content of the carboxyvinyl polymer is 12.7% by mass (% by mass based on the total mass of all ingredients excluding a solvent in the coating; the same applies below), the content of the calcium chloride is 0.5% by mass, the content of the xanthan gum is 25.3% by mass, the content of the sucralose is 0.8% by mass, the content of the HPMC is 15.2% by mass, the content of the erythritol is 35.4% by mass, and the content of the HPC is 10.1% by mass.

[10-3] The oral composition according to [10-1] above, wherein
in the tablet core, the content of levofloxacin hydrate is 69.7% by mass (% by mass based on the total mass of all ingredients excluding a solvent in the tablet core; the same applies below), the content of the crystalline cellulose is 6.2% by mass, the content of the sodium carboxymethyl starch is 17.7% by mass, the content of the pregelatinized starch is 2.7% by mass, and the content of the sodium stearyl fumarate is 3.7% by mass, in the seal coating, the content of the HPMC is 95.2% by mass (% by mass based on the total mass of all ingredients excluding a solvent in the seal coating; the same applies below), and the content of the macrogol 6000 (trade name) is 4.8% by mass, and
in the coating, the content of the carboxyvinyl polymer is 9.4% by mass (% by mass based on the total mass of all ingredients excluding a solvent in the coating; the same applies below), the content of the calcium chloride is 0.4% by mass, the content of the xanthan gum is 26.3% by mass, the content of the sucralose is 0.9% by mass, the content of the HPMC is 15.8% by mass, the content of the erythritol is 36.8% by mass, and the content of the HPC is 10.5% by mass.

The oral composition of the tenth aspect of the present invention has a favorable slipping property and favorable swallowability without adhesion to the mucosa. Otherwise, an effect of masking an unpleasant taste caused by the levofloxacin hydrate as an active ingredient can be obtained. Preferably, the present oral composition has both of the two above effects. The oral composition in a further preferred aspect has an improved drug-dissolution property.

Still further, an eleventh aspect of the present invention relates to the following oral composition.

[11-1] An oral composition having:
a tablet core (preferably a mini-tablet) comprising valaciclovir hydrochloride as an active ingredient, and
(i) partially pregelatinized starch (e.g. PCS (trade name)), sodium carboxymethyl starch, pregelatinized starch (e.g. SWELSTAR WB-1 (trade name)), talc, and sodium stearyl fumarate, or (ii) partially pregelatinized starch (e.g. PCS (trade name)), pregelatinized starch (e.g. SWELSTAR WB-1 (trade name)), talc, and sodium stearyl fumarate;
over the tablet core,
a seal coating comprising (iii) pregelatinized starch (e.g. SWELSTAR WB-1 (trade name)) and erythritol, or (iv) HPMC (e.g. TC-5E (trade name)) and erythritol; and
over the seal coating,
a coating comprising a carboxyvinyl polymer (e.g. Carbopol 974P (trade name)), calcium chloride, xanthan gum, sucralose, HPMC (e.g. TC-5E (trade name)), erythritol, and HPC (e.g. HPC-L (trade name)).

[11-2] The oral composition according to [11-1] above, wherein
in the tablet core, the content of the valaciclovir hydrochloride is 75.6% by mass (% by mass based on the total mass of all ingredients excluding a solvent in the tablet core; the same applies below), the content of the partially pregelatinized starch is 4.6% by mass, the content of the sodium carboxymethyl starch is 13.6% by mass, the content of the pregelatinized starch is 2.0% by mass, the content of the talc is 2.7% by mass, and the content of the sodium stearyl fumarate is 1.4% by mass,
in the seal coating, the content of the erythritol is 90% by mass (% by mass based on the total mass of all ingredients excluding a solvent in the seal coating; the same applies below), and the content of the pregelatinized starch is 10% by mass, and
in the coating, the content of the carboxyvinyl polymer is 16.7% by mass (% by mass based on the total mass of all ingredients excluding a solvent in the coating; the same applies below), the content of the calcium chloride is 0.6% by mass, the content of the xanthan gum is 23.4% by mass, the content of the sucralose is 0.8% by mass, the content of the HPMC is 13.9% by mass, the content of the erythritol is 33.4% by mass, and the content of the HPC is 11.1% by mass.

[11-3] The oral composition according to [11-1] above, wherein
in the tablet core, the content of the valaciclovir hydrochloride is 75.6% by mass (% by mass based on the total mass of all ingredients excluding a solvent in the tablet core; the same applies below), the content of the partially pregelatinized starch is 18.7% by mass, the content of the pregelatinized starch is 1.5% by mass, the content of the talc is 2.7% by mass, and the content of the sodium stearyl fumarate is 1.4% by mass, in the seal coating, the content of the HPMC is 29.4% by mass (% by mass based on the total mass of all ingredients excluding a solvent in the seal coating; the same applies below), and the content of the erythritol is 70.6% by mass, and in the coating, the content of the carboxyvinyl polymer is 9.3% by mass (% by mass based on the total mass of all ingredients excluding a solvent in the coating; the same applies below), the content of the calcium chloride is 0.2% by mass, the content of the xanthan gum is 26.1% by mass, the content of the sucralose is 0.9% by mass, the content of the HPMC is 15.5% by mass, the content of the erythritol is 37.3% by mass, and the content of the HPC is 10.6% by mass.

The oral composition of the eleventh aspect of the present invention has a favorable slipping property and favorable swallowability without adhesion to the mucosa. Otherwise, an effect of masking an unpleasant taste caused by the valaciclovir hydrochloride as an active ingredient can be obtained. Preferably, the present oral composition has both of the two above effects. The oral composition in a further preferred aspect has an improved drug-dissolution property.

Advantageous Effects of Invention

In the case of a composition having the preferred coating of the present invention, the surface layer of a tablet rapidly turns into a gel in the presence of a small amount of water or saliva. At the same time, a first thickener that is a metal crosslinked thickener, and preferably, a first thickener such as a carboxyvinyl polymer and/or sodium alginate is crosslinked by polyvalent metal ions generated from a polyvalent metal compound, and viscosity thereby increases. As a result, a relatively hard jelly-like gel is formed, so that the tablet easily slips on the mucosa, and its swallowability is improved. Moreover, since the gelatinous coating film suppresses short-term drug dissolution before the swallowing of the tablet, it can be anticipated that the effect of masking an unpleasant taste can be obtained. Furthermore, a composition having the preferred coating of the present invention can be anticipated to have an improved dissolution property in that it is rapidly disintegrated and thus it does not affect the dissolution of a drug after it has been swallowed. The coating composition of the present invention has at least one of, and preferably, all of the above-described preferred properties. When a high-dose preparation is produced, a more preferred coating composition of the present invention can be used to produce a preparation having an improved administering property, without affecting drug dissolution. A particularly preferred coating composition of the present invention can be anticipated to have a further improved effect of masking an unpleasant taste.

Further, using a preferred coating composition of the present invention, a coated preparation can be easily obtained according to a common coating technique.

Description of Embodiments

The present invention will be described in detail below.
The first thickener used in the present invention is a metal-crosslinked thickener. The metal-crosslinked thickener means a substance, which is crosslinked by polyvalent metal ions that are generated from a polyvalent metal compound in the presence of a small amount of water, and which is not crosslinked in the absence of water (in the presence of an alcohol solvent or the like) because polyvalent metal ions are not generated from the polyvalent metal compound. The type of the metal-crosslinked thickener is not particularly limited, as long as it exhibits the aforementioned properties. Specific examples of such a metal-crosslinked thickener include a carboxyvinyl polymer, sodium alginate, polyacrylic acid, polymethacrylic acid, pectin, carboxymethylcellulose, glucomannan, and carmellose sodium. Preferred examples include a carboxyvinyl polymer and sodium alginate, a carboxyvinyl polymer is more preferable. As a result of this crosslinking formation, viscosity increases, and a relatively hard jelly-like gel is formed. Thereby, it can be anticipated that the preparation easily slips on the mucosa upon administration and swallowability is improved, and that the effect of masking an unpleasant taste can be obtained by suppressing short-term drug dissolution before the swallowing of the preparation, as described later.

The type of the carboxyvinyl polymer used in the present invention is not particularly limited. A carboxyvinyl polymer having an indicated viscosity of 4000 to 60000 mPa·s (0.5%, 25° C., 20 rpm) can be preferably used. A carboxyvinyl polymer having an indicated viscosity of 4000 to 40000 mPa·s is more preferable because it hardly causes a delay in dissolution. More specific examples of such a carboxyvinyl polymer that can be used herein include commercially available products such as Carbopol 971P (trade name) (Lubrizol Advanced Material Inc.; indicated viscosity: 6420 mPa·s), Carbopol 974P (trade name) (Lubrizol Advanced Material Inc.; indicated viscosity: 32850 mPa·s), HIVISWAKO 103 (trade name) (Wako Pure Chemical Industries, Ltd.; indicated viscosity: 15000 mPa·s), HIVISWAKO 104 (trade name) (Wako Pure Chemical Industries, Ltd.; indicated viscosity: 26000 mPa·s), and HIVISWAKO 105 (trade name) (Wako Pure Chemical Industries, Ltd.; indicated viscosity: 4000 mPa·s).

The type of the sodium alginate used in the present invention is not particularly limited. Sodium alginate having an indicated viscosity of 600 mPa·s or more (1%/1% KCl solution, 25° C.) can be preferably used. Sodium alginate having an indicated viscosity of 800 to 1600 mPa·s is more preferable. More specific examples of such sodium alginate that can be used herein include commercially available products such as Kimica Algin 1-8 (KIMICA Corporation; indicated viscosity, 800 to 900 mPa·s (1%, 20° C.)) and Duck Algin (trade name) (Kibun Food Chemifa Co., Ltd.; indicated viscosity: 850 mPa·s).

The first thickener such as a carboxyvinyl polymer or sodium alginate is a metal-crosslinked thickener, which is crosslinked by polyvalent metal ions generated from the after-mentioned polyvalent metal compound in the presence of water, and as a result, the viscosity of the first thickener increases, thereby forming a relatively hard jelly-like gel. Preferably, the carboxyvinyl polymer and the sodium alginate contained in the composition of the present invention are not substantially crosslinked by polyvalent metal ions. The content of such a carboxyvinyl polymer or sodium alginate is preferably 3% to 15% by mass, and more preferably 10% to 13% by mass, based on the total mass of all ingredients excluding a solvent in the coating composition of the present invention. Otherwise, the content of such a carboxyvinyl polymer or sodium alginate is preferably 3% to 20% by mass, more preferably 3% to 15% by mass or 8% to 18% by mass, and further preferably 9% to 17% by mass, based on the total mass of all ingredients excluding a solvent in the coating composition of the present invention. The ratio of such a carboxyvinyl polymer or sodium alginate based on the total mass of all ingredients in the coating used for the oral composition of the present invention (hereinafter referred to as a coating film at times) is the same as described above.

In the present specification, the polyvalent metal compound means pharmaceutically acceptable water-soluble salts of polyvalent metals such as calcium, magnesium, aluminum and zinc. Specific examples of such a polyvalent metal compound include calcium chloride, magnesium chloride, aluminum chloride, aluminum sulfate, aluminum potassium sulfate, aluminum ferric chloride, ammonium alum, ferric sulfate, aluminum hydroxide, aluminum silicate, aluminum phosphate, iron citrate, magnesium oxide, calcium oxide, zinc oxide, zinc sulfate, and a hydrate thereof. Preferred examples include calcium chloride and a hydrate thereof. A calcium chloride dihydrate is more preferable. Specific examples of polyvalent metal ions generated from such a polyvalent metal compound include calcium ions, magnesium ions, aluminum ions, divalent or trivalent iron ions, and zinc ions. Calcium ions are preferable.

The polyvalent metal compound used in the present invention is preferably mixed at a mass percentage of 2% to 15%, and more preferably 2% to 11%, based on the mass of the first thickener selected from the group consisting of a carboxyvinyl polymer and sodium alginate. Otherwise, the polyvalent metal compound used in the present invention is preferably mixed at a mass percentage of 0.1% to 1% by mass, and more preferably 0.2% to 0.7% by mass, based on the total mass of all ingredients excluding a solvent in the coating composition of the present invention.

The type of the xanthan gum used in the present invention is not particularly limited. Xanthan gum having an indicated viscosity of 600 mPa·s or more (1%/1% KCl solution, 25° C.) can be preferably used. Xanthan gum having an indicated viscosity of 800 to 1600 mPa·s is more preferable. More specific examples of such xanthan gum that can be used herein include commercially available products such as Keltrol CG-T (trade name) (Sansho Co., Ltd.; indicated viscosity: 1555 mPa·s), and San-Ace (trade name) (San-Ei Gen F. F. I., Inc.; indicated viscosity: 1600 mPa·s).

The type of the guar gum used in the present invention is not particularly limited. Guar gum having an indicated viscosity of 600 mPa·s or more (1%/1% KCl solution, 25° C.) can be preferably used. Guar gum having an indicated viscosity of 800 to 1600 mPa·s (1%/1% KCl solution, 25° C.) is more preferable. More specific examples of such guar gum that can be used herein include commercially available products such as guar gum RG100 (trade name) (MRC Polysaccharide Co., Ltd.; indicated viscosity: 1100 mPa·s). In addition, VIS TOP D-2029 (trade name) (San-Ei Gen F. F. I., Inc.; indicated viscosity: approximately 450 mPa·s (0.5%)) can also be used.

Xanthan gum, guar gum and sodium alginate are second thickeners. By adding such a second thickener, a moderate adhesive property is generated among tablets, and it causes good cohesiveness of tablets in the oral cavity, so that the tablets can be easily swallowed. The content of at least one type of a second thickener selected from the group consisting of xanthan gum, guar gum and sodium alginate in the coating film can be appropriately adjusted depending on the composition of other ingredients. In order to obtain a good administering property, the content of the second thickener is preferably 10% to 40% by mass, and more preferably 20% to 30% by mass.

Examples of a combination of the first thickener with the second thickener in the coating composition and oral composition of the present invention will be given below, with the proviso that when the first thickener is sodium alginate the second thickener is not sodium alginate:

(1) a combination of the first thickener: a carboxyvinyl polymer with the second thickener: xanthan gum;

(2) a combination of the first thickener: a carboxyvinyl polymer with the second thickener: guar gum;

(3) a combination of the first thickener: a carboxyvinyl polymer with the second thickener: sodium alginate;

(4) a combination of the first thickener: a carboxyvinyl polymer with the second thickener: xanthan gum and guar gum;

(5) a combination of the first thickener: a carboxyvinyl polymer with the second thickener: xanthan gum and sodium alginate;

(6) a combination of the first thickener: a carboxyvinyl polymer with the second thickener: guar gum and sodium alginate;

(7) a combination of the first thickener: a carboxyvinyl polymer with the second thickener: xanthan gum, guar gum and sodium alginate;

(8) a combination of the first thickener: sodium alginate with the second thickener: xanthan gum;

(9) a combination of the first thickener: sodium alginate with the second thickener: guar gum; and

(10) a combination of the first thickener: sodium alginate with the second thickener: xanthan gum and guar gum.

Examples of the combination of the first thickener with the second thickener in a preferred aspect of the present invention will be given below:

(1) a combination of the first thickener: a carboxyvinyl polymer with the second thickener: xanthan gum;

(2) a combination of the first thickener: a carboxyvinyl polymer with the second thickener: guar gum;

(3) a combination of the first thickener: a carboxyvinyl polymer with the second thickener: sodium alginate;

(4) a combination of the first thickener: sodium alginate with the second thickener: xanthan gum; and (5) a combination of the first thickener: sodium alginate with the second thickener: guar gum.

The combination of the first thickener with the second thickener in a more preferred aspect of the present invention is (1) a combination of the first thickener: a carboxyvinyl polymer with the second thickener: xanthan gum.

The surface layer of an oral composition (e.g. a tablet, etc.), which is coated with a coating composition comprising a first thickener selected from the group consisting of a carboxyvinyl polymer and sodium alginate, a polyvalent metal compound, and at least one type of a second thickener selected from the group consisting of xanthan gum, guar gum and sodium alginate, rapidly turns into a gel in the presence of a small amount of water or saliva. At the same time, the carboxyvinyl polymer and/or the sodium alginate are crosslinked by polyvalent metal ions generated from the polyvalent metal compound, and as a result, viscosity increases and a relatively hard jelly-like gel is thereby formed. Thus, the oral composition easily slips on the mucosa, and swallowability is improved. Simultaneously, the gelled film suppresses short-term drug dissolution before the swallowing of the oral composition, so as to exhibit an unpleasant taste-masking effect. When the oral composition is used for the after-mentioned multi-unit, cohesiveness of tablets in the oral cavity becomes better, and swallowability is further improved.

The sucralose used in the present invention is a sweetener that is widely used instead of sucrose. The content of the sucralose in the coating film is preferably 0.01% to 5% by mass, and more preferably 0.5% to 1% by mass or 0.1% to 2% by mass (% by mass based on the total mass of all ingredients excluding a solvent in the coating film). The sucralose that can be used in the present invention is considered to exhibit an effect of further improving the unpleasant taste-masking effect.

The sugar or sugar alcohol that can be used in the present invention has a solubility at 20° C. of 30 or more, and preferably of 50 or more. The solubility means the largest mass (g) of a solute dissolved in 100 g of water. Examples of preferred sugar or sugar alcohol that can be used in the present invention include trehalose, maltose, erythritol, and maltitol. Erythritol and maltitol that cause a moderate sweet taste when they are placed in the mouth are preferable in terms of good sensation upon administration. In addition, erythritol, maltitol and trehalose have low moisture absorbency, and thus, they are particularly preferable in terms of the preservation stability of a preparation. The content of the sugar or sugar alcohol in the coating film is preferably 10% to 50% by mass, and more preferably 30% to 40% by mass (% by mass based on the total mass of all ingredients excluding a solvent in the coating film).

The sugar or sugar alcohol having a solubility at 20° C. of 30 or more that can be used in the present invention accelerates the swelling of the gel by the thickener. It is considered that the sugar or sugar alcohol also promotes the disintegration of the gel and exhibits the effect of improving a drug-dissolution property.

The type of the HPMC used in the present invention is not particularly limited. HPMC having a viscosity of 100 mPa·s or less is preferable, and HPMC having a viscosity of 10 mPa·s or less is more preferable. More specific examples of such HPMC that can be used herein include commercially available products such as TC-5E (trade name) (Shin-Etsu Chemical Co., Ltd.; indicated viscosity: 3 mPa·s) and TC-5R (trade name) (Shin-Etsu Chemical Co., Ltd.; indicated viscosity: 6 mPa·s).

The content of the HPMC in the coating film is preferably 5% to 35% by mass, more preferably 10% to 30% by mass, and further preferably 10% to 20% by mass or 13% to 25% by mass (% by mass based on the total mass of all ingredients excluding a solvent in the coating film).

A combined use of the HPMC with the sugar or sugar alcohol having a solubility at 20° C. of 30 or more in the oral cavity promotes the disintegration of the gel, as compared with a single use of the sugar or sugar alcohol. Thereby, when the gel needs to be rapidly disintegrated, a simple increase in the amount of the sugar or sugar alcohol can be avoided.

As described above, a combined use of the HPMC with the sugar or sugar alcohol having a solubility at 20° C. of 30 or more brings on a synergistic effect, and it promotes the disintegration of the gel. Thereby, when the drug core is coated with the gel, a drug-dissolution property is effectively improved. The mixing ratio (mass ratio) between the HPMC and the sugar or sugar alcohol is preferably 1:1 to 1:4, and more preferably 1:2 to 1:3.

The thickener used in the fifth to eighth aspects of the present invention means a substance that turns into a gel when it is allowed to come into contact with water. The type of the thickener is not particularly limited, as long as it has such a property. Examples of such a thickener include the metal-crosslinked thickeners and second thickeners, which are described in the first to fourth aspects of the present invention. More specific examples of such a thickener include a carboxyvinyl polymer, xanthan gum, starch and a derivative thereof, agar, sodium alginate, arabinogalactan, galactomannan, cellulose and a derivative thereof, carrageenan, dextran, tragacanth, gelatin, pectin, hyaluronic acid, guar gum, gellan gum, collagen, and casein.

The thickener may be used singly or in combination of several types. A combination of two or more types of thickeners including a metal-crosslinked thickener is preferable. A preferred example of the combination of two or more types of thickeners including a metal-crosslinked thickener is a combination of one or more types selected from the group consisting of a carboxyvinyl polymer and sodium alginate, used as metal-crosslinked thickener(s), with one or more types selected from the group consisting of xanthan gum, guar gum and sodium alginate, with the proviso that a combination of the same substances is excluded.

The coating composition of the present invention and the oral composition of the present invention having the coating may also comprise hydroxypropylcellulose (hereinafter also referred to as HPC) and the like. Since HPC provides appropriate viscosity when it is dissolved in alcohol, it is able to suppress rapid sedimentation of particles, when the coating composition is dispersed into ethanol and spray-coating is then performed. Thus, the use of such hydroxypropylcellulose is advantageous in order to maintain uniformity. Moreover, hydroxypropylcellulose acts as a binder to help adhesion of particles to the surface of a tablet, so as to enhance coating efficiency, and it also acts to form a smooth film. For such reasons, addition of a certain amount of HPC to the coating composition is advantageous for the production of an oral composition having the coating.

The type of the HPC that can be used in the present invention is not particularly limited. Hydroxypropylcellulose having low viscosity is preferable, and hydroxypropylcellulose having a viscosity of 10 mPa·s (2%, 20° C.) or less is more preferable. More specific examples of such HPC include commercially available products such as HPC-L (trade name) (Nippon Soda Co., Ltd.; indicated viscosity: 6.0 to 10 mPa·s), and HPC-SL (trade name) (Nippon Soda Co., Ltd.; indicated viscosity: 3.0 to 5.9 mPa·s). The content of the HPC in the coating film is preferably 0.1% to 15% by mass, and more preferably 5% to 15% by mass or 0.1% to 12% by mass (% by mass based on the total mass of all ingredients excluding a solvent in the coating film). The content of the HPC in the coating composition (coating solution) of the present invention used for spray-coating is 0.1% to 5% by mass, preferably 0.2% to 3% by mass, and more preferably 0.5% to 1.8% by mass, based on the total mass of the coating solution.

As a solvent that can be used to prepare the coating composition of the present invention, water, alcohol, a mixed solvent of water and alcohol, or the like can be used. Of these, alcohol is preferable. As such alcohol, ethanol or dehydrated ethanol is preferable. Herein, the term "ethanol" means a substance containing 95.1 to 96.9 vol % or more of ethanol ($C_2H_6O$), and the term "dehydrated ethanol" means a substance containing 99.5 vol % or more of ethanol. Preferably, it is 95.1 to 96.9 vol % or more of ethanol.

Glycerin may be added to prepare the coating composition of the present invention. It is considered that glycerin acts as a plasticizer in the coating composition, and that it has the effect of promoting the swelling of a gel when the coating film is allowed to come into contact with water. The type of the glycerin used in the composition of the present invention is not particularly limited. It is preferable to use concentrated glycerin containing 98.0% or more of glycerin with respect to a dehydration product converted during assay. When glycerin is added to the coating composition, the content of the glycerin is 0.1% to 5% by mass, preferably 0.5% to 3% by mass, and more preferably 0.5% to 1% by mass, based on the total mass of the coating composition including a solvent.

It is to be noted that, in the preparation of the coating composition, an aqueous solvent such as water or a mixed solvent of water and alcohol can be used depending on the type or amount of a thickener used. When an aqueous solvent is used to prepare the coating composition of the present invention, if the concentration of the coating composition is set at high, viscosity becomes high, resulting in poor operability in some cases. Thus, it is necessary to select a coating method, as appropriate, depending on the properties of the coating composition.

The coating compositions of the several aspects of the present invention each comprise:

a carboxyvinyl polymer (e.g. Carbopol 974P (trade name)) as a first thickener;

calcium chloride as a polyvalent metal compound;

xanthan gum as a second thickener;

sucralose;

HPMC (e.g. TC-5E (trade name));

erythritol as sugar or sugar alcohol having a solubility at 20° C. of 30 or more;

HPC (e.g. HPC-L (trade name)); and ethanol as a solvent.

Preferably, in the above-described coating composition, the content of the carboxyvinyl polymer is 3% to 20% by mass and more preferably 9% to 17% by mass (% by mass based on the total mass of all ingredients excluding a solvent; the same applies below), the content of the calcium chloride is 0.1% to 1% by mass and more preferably 0.2% to 0.7% by mass, the content of the xanthan gum is 10% to 40% by mass and more preferably 20% to 30% by mass, the content of the sucralose is 0.01% to 5% by mass and more preferably 0.5% to 1% by mass, the content of the HPMC is 5% to 35% by mass and more preferably 10% to 20% by mass, the content of the erythritol is 10% to 50% by mass and more preferably 30% to 40% by mass, and the content of the HPC is 0.1% to 15% by mass and more preferably 5% to 15% by mass.

In a more preferred embodiment, in the above-described coating composition, the content of the carboxyvinyl polymer is 12.7% by mass (% by mass based on the total mass of all ingredients excluding a solvent; the same applies below), the content of the calcium chloride is 0.5% by mass, the content of the xanthan gum is 25.3% by mass, the content of the sucralose is 0.8% by mass, the content of the HPMC is 15.2% by mass, the content of the erythritol is 35.4% by mass, and the content of the HPC is 10.1% by mass.

In another preferred embodiment, in the above-described coating composition, the content of the carboxyvinyl polymer is 9.4% by mass (% by mass based on the total mass of all ingredients excluding a solvent; the same applies below), the content of the calcium chloride is 0.4% by mass, the content of the xanthan gum is 26.3% by mass, the content of the sucralose is 0.9% by mass, the content of the HPMC is 15.8% by mass, the content of the erythritol is 36.8% by mass, and the content of the HPC is 10.5% by mass.

In another preferred embodiment, in the above-described coating composition, the content of the carboxyvinyl polymer is 16.7% by mass (% by mass based on the total mass of all ingredients excluding a solvent; the same applies below), the content of the calcium chloride is 0.6% by mass, the content of the xanthan gum is 23.4% by mass, the content of the sucralose is 0.8% by mass, the content of the HPMC is 13.9% by mass, the content of the erythritol is 33.4% by mass, and the content of the HPC is 11.1% by mass.

In another preferred embodiment, in the above-described coating composition, the content of the carboxyvinyl polymer is 9.3% by mass (% by mass based on the total mass of all ingredients excluding a solvent; the same applies below), the content of the calcium chloride is 0.2% by mass, the content of the xanthan gum is 26.1% by mass, the content of the sucralose is 0.9% by mass, the content of the HPMC is 15.5% by mass, the content of the erythritol is 37.3% by mass, and the content of the HPC is 10.6% by mass.

As a method of preparing the coating composition of the first aspect of the present invention, constitutional gradients of the coating composition of the present invention may be dissolved in or uniformly dispersed into water, alcohol, a mixed solvent of water and alcohol, or the like. There is preferably applied a method of uniformly dispersing constitutional ingredients other than a polyvalent metal compound into an alcohol solution in which the polyvalent metal compound has been dissolved. Specifically, the coating composition may be prepared by uniformly dispersing fine powders comprising at least one second thickener selected from the group consisting of xanthan gum, guar gum and sodium alginate (preferably, xanthan gum), and a first thickener selected from the group consisting of a carboxyvinyl polymer and sodium alginate (preferably, a carboxyvinyl polymer), with the proviso that when the first thickener is sodium alginate the second thickener is not sodium alginate, and preferably, further (i) HPMC and/or sugar or sugar alcohol having a solubility at 20° C. of 30 or more, or further (ii) at least one type selected from the group consisting of sucralose, HPMC, and sugar or sugar alcohol having a solubility at 20° C. of 30 or more, into an alcohol solution in which a polyvalent metal compound has been dissolved. More preferably, ethanol is used as a solvent.

Further preferably, fine powders comprising: at least one second thickener selected from the group consisting of xanthan gum, guar gum and sodium alginate (more preferably, xanthan gum); a first thickener that is a metal-cross-linked thickener (more preferably, a thickener selected from the group consisting of a carboxyvinyl polymer and sodium alginate, and further preferably, a carboxyvinyl polymer), with the proviso that when the first thickener is sodium alginate the second thickener is not sodium alginate; HPMC; and sugar or sugar alcohol having a solubility at 20° C. of 30 or more, are uniformly dispersed in a mixed solution of ethanol and glycerin, so as to prepare a suspension, separately. Then, a solution formed by dissolving a polyvalent metal compound in ethanol is added to the thus obtained suspension, so as to prepare a coating solution.

Still further preferably, fine powders comprising: at least one second thickener selected from the group consisting of xanthan gum, guar gum and sodium alginate (more preferably, xanthan gum); a first thickener that is a metal-cross-linked thickener (more preferably, a thickener selected from the group consisting of a carboxyvinyl polymer and sodium alginate, and further preferably, a carboxyvinyl polymer), with the proviso that when the first thickener is sodium alginate the second thickener is not sodium alginate; sucralose; HPMC; and sugar or sugar alcohol having a solubility at 20° C. of 30 or more, are uniformly dispersed in a mixed solution of ethanol and glycerin, so as to prepare a suspension, separately. Then, a solution formed by dissolving a polyvalent metal compound in ethanol is added to the thus obtained suspension, so as to prepare a coating solution.

As a method of preparing the coating composition of the fifth aspect of the present invention, fine powders comprising HPMC and sugar or sugar alcohol having a solubility at 20° C. of 30 or more are dissolved in or uniformly dispersed into a suspension or solution, in which thickeners have been dispersed or dissolved, so as to prepare a coating solution. As described above, alcohol is preferably used as a solvent. Ethanol is more preferably used.

In order to obtain a suspension in which the coating composition of the present invention has been uniformly dispersed, the particle diameter of constitutional ingredients is preferably reduced using a mill such as a jet mill, as necessary. With regard to particle diameter, a median diameter (D50: the diameter causing that, when powders are divided into two portions based on a certain particle diameter, the amount of the greater portion becomes equal to the amount of the smaller portion) is preferably 35 µm or less, more preferably 25 µm or less, and further preferably 10 µm or less.

As a method of coating a drug core or an orally-administered solid with the coating composition of the present invention, a known coating technique can be applied. Thus, the coating method is not particularly limited. Examples of a coating device that can be applied herein include a pan coating device, a fluidized bed coating device, and a vented rotating-drum coating device. A vented rotating-drum coating device is particularly suitable for the after-mentioned coating of mini-tablets. Spray-coating or powder-coating is carried out using these devices, so that a drug core or an orally-administered solid can be coated with the present coating composition. A preferred coating method is spray-coating. It is particularly preferable to continuously supply the present coating composition using a spray nozzle. A drug core or an orally-administered solid can be coated by a single coating operation. However, the number of coating operations is not limited to one, but coating operations may be carried out several times.

As with the above-described preferred example, if alcohol is used as a solvent, the first thickener such as a carboxyvinyl polymer or sodium alginate is not substantially crosslinked by polyvalent metal ions, and as a result, a coating composition having low viscosity can be obtained. Thus, spray-coating can be easily carried out using such a coating composition having low viscosity. In addition, since the used solvent is an alcohol solution, a drying operation can be carried out in a short time after completion of the coating operation, and thus it is advantageous for production.

When the oral composition of the second aspect of the present invention is obtained with the use of the above-described coating using alcohol as a solvent, the first thickener contained in the coating film, such as a carboxyvinyl polymer or sodium alginate, is not substantially crosslinked by polyvalent metal ions, if the film is not allowed to come into contact with water.

It is also possible to produce an oral composition using water as a solvent. When water is used as a solvent, the first thickener such as a carboxyvinyl polymer or sodium alginate is substantially crosslinked by polyvalent metal ions, and as a result, a coating composition having high viscosity can be obtained. Thus, when a drug core or an orally-administered solid is coated with this coating composition having high viscosity, the oral composition of the ninth aspect of the present invention, which comprises a gelatinous substance selected from the group consisting of a carboxyvinyl polymer crosslinked by polyvalent metal ions, sodium alginate crosslinked by polyvalent metal ions, and the like, can be produced.

The amount of the solid ingredients of the coating composition of the present invention is preferably 2% to 30% by mass, and more preferably 3% to 15% by mass, based on the mass of the drug core or orally-administered solid to be coated. The thickness of the coating film of the thus coated oral composition is 10 µm to 100 µm, and preferably 20 µm to 70 µm.

When the first thickener selected from the group consisting of a carboxyvinyl polymer and sodium alginate of the coating composition (coating solution) of the present invention used for spray-coating is present in the coating solution, the content thereof is, for example, 0.5% to 5% by mass, preferably 0.5% to 4% by mass, and more preferably 0.5% to 3% by mass, based on the total mass of the coating solution.

When at least one type of the second thickener selected from the group consisting of xanthan gum, guar gum and sodium alginate is present in the coating solution, the content thereof is, for example, 1% to 5% by mass, preferably 1% to 4% by mass, and more preferably 3% to 4% by mass, based on the total mass of the coating solution.

When the thickeners are present in the coating solution, the total content of the thickeners is, for example, 1.5% to 10% by mass, preferably 1.5% to 8% by mass, and more preferably 3.5% to 7% by mass, based on the total mass of the coating solution.

When the HPMC is present in the coating solution, the content thereof is 1% to 10% by mass, preferably 1% to 5% by mass, and more preferably 1.5% to 3.5% by mass, based on the total mass of the coating solution.

When the sugar or sugar alcohol having a solubility at 20° C. of 30 or more is present in the coating solution, the content thereof is 1% to 10% by mass, preferably 1% to 6% by mass, and more preferably 3% to 6% by mass, based on the total mass of the coating composition (coating solution) of the present invention used for the spray-coating.

When the sucralose is present in the coating solution, the content thereof is 0.001% to 0.7% by mass, preferably 0.01% to 0.3% by mass, and more preferably 0.05% to 0.2% by mass, based on the total mass of the coating solution.

The coating composition of the present invention includes: a kit comprising a combination of ingredients to be contained in the coating composition; and a combination or kit of compositions, in which ingredients to be contained in the coating composition are divided into two or more groups. An example of such a combination or kit is a combination of a coating composition (A) comprising a first thickener, a second thickener, and as necessary, (i) HPMC and sugar or sugar alcohol having a solubility at 20° C. of 30 or more, or (ii) at least one type selected from the group consisting of sucralose, HPMC, and sugar or sugar alcohol having a solubility at 20° C. of 30 or more, with a coating composition (B) comprising a polyvalent metal compound. Other examples of such a combination or kit include: a kit, in which the above-described coating composition (A) is combined with a polyvalent metal compound (C); a kit, in which a combined composition (D) of the first thickener and the second thickener, a coating composition (E) comprising HPMC and sugar or sugar alcohol having a solubility at 20° C. of 30 or more, and a polyvalent metal compound (C) are combined; and a kit, in which a coating composition (E') comprising at least one type selected from the group consisting of a combined composition (D) of the first thickener and the second thickener, sucralose, HPMC, and sugar or sugar alcohol having a solubility at 20° C. of 30 or more is combined with a polyvalent metal compound (C).

A drug core or an orally-administered solid may be coated as described above, with the combined one of ingredients contained in such a combination or kit. Also, a drug core or an orally-administered solid may be successively coated with each coating composition that has been dissolved in or uniformly dispersed into an alcohol solvent or water. During the coating operations, the solvents may be changed. In the aforementioned example, the drug core or the orally-administered solid may be first coated with the composition (A) that has been dissolved in or uniformly dispersed into an alcohol solvent, and may be then coated with the composition (B) that has been dissolved in water. In this case, the oral composition of the ninth aspect of the present invention comprising a coating, in which the first thickener is partially crosslinked by polyvalent metal ions, is produced at the boundary between the composition (A) and the composition (B).

The oral composition of the second aspect of the present invention can be obtained by coating a drug core with the coating composition of the first aspect of the present invention. However, the method for producing the oral composition of the second aspect of the present invention is not limited thereto. Any oral composition, which has a first thickener such as a carboxyvinyl polymer or sodium alginate, a polyvalent metal compound, and a second thickener such as xanthan gum, guar gum or sodium alginate, with the proviso that when the first thickener is sodium alginate the second thickener is not sodium alginate, over the surface of a drug core, is included in the oral composition of the second aspect of the present invention.

The oral composition of the sixth aspect of the present invention can be obtained by coating a drug core with the coating composition of the fifth aspect of the present invention. However, the method for producing the oral composition of the sixth aspect of the present invention is not limited thereto. Any oral composition, which has thickeners, sugar or sugar alcohol having a solubility at 20° C. of 30 or more, and HPMC over the surface of a drug core, is included in the oral composition of the sixth aspect of the present invention.

Examples of the drug core containing an active ingredient used in the oral composition of the present invention include solid preparations such as a tablet core, a pill core, a capsule core, a pellet core and a granule core. The type of the orally-administered solid is not particularly limited, as long as it is a solid product that contains a drug core as a solid and is used for oral administration. In the case of a high-dose preparation, in order to prevent the preparation from growing in size, a mini-tablet, in which the content of a drug per tablet can be decreased and the bulk is reduced to the minimum, is preferably applied as a drug core. Such a mini-tablet can be produced in ordinary equipment.

The mini-tablet used in the present specification is a form of a tablet, and it is referred to as a granular solid preparation having a diameter and a thickness, each of which is 6 mm or less. In the case of a high-dose active ingredient, if the diameter of a tablet is 3 to 4 mm, the number of tablets for a single administration may be approximately 20 to 100. In the present specification, a single administration of an oral preparation, in which the number of tablets for the single administration is 10 or more, is referred to as a multi-unit. It is preferably a granular tablet having a diameter and a thickness, each of which is 0.5 to 5 mm, and more preferably 2 to 4 mm.

In the oral composition of the present invention, a seal coating may be established between a drug core or orally-administered solid containing an active ingredient and a coating (which may be referred to as "over-coating" in the present specification). The oral composition of the present invention having such a seal coating can be obtained, for example, by coating a seal-coated drug core having a seal coating with the coating composition of the present invention.

It is anticipated that the seal coating of a drug core is useful to prevent the phenomenon whereby the ingredients of the drug core are moved to the coating layer during preservation and incompatibility thereby occurs between the ingredients of the drug core and the ingredients of the coating layer, or to prevent the phenomenon whereby unpleasant taste ingredients contained in the drug core are moved to the coating layer during preservation and the unpleasant taste-masking effect of the coating is thereby attenuated upon administration, or to enhance the unpleasant taste-masking effect of the coating upon administration.

The present seal coating is obtained by coating a drug core containing an active ingredient with a seal coating composition according to a known coating technique. The type of such a seal coating composition is not particularly limited, as long as it is able to prevent ingredients contained in the drug core from moving to the coating during preservation of the oral composition. An example of such a seal coating composition is a composition comprising (i) at least one selected from the group consisting of HPMC, HPC, ethylcellulose, polyvinylpyrrolidone, Pullulan, an acrylate-methacrylate copolymer and the like, or (ii) at least one selected from the group consisting of HPMC, HPC, ethylcellulose, polyvinylpyrrolidone, Pullulan, an acrylate-methacrylate copolymer, pregelatinized starch, erythritol, magrogol 6000 (trade name), talc, light anhydrous silicic acid and the like.

As a solvent that can be used to prepare the seal coating composition, water, alcohol, a mixed solvent of water and alcohol, etc. can be used.

The amount of solid ingredients contained in the seal coating composition is preferably 1% to 10% by mass, and more preferably 2% to 5% by mass, based on the mass of the drug core or orally-administered solid to be coated. The thickness of the seal coating film of the oral composition comprising the thus obtained seal coating is 10 to 80 μm, and preferably 20 to 40 μm.

The oral compositions of several embodiments of the present invention do not have a seal coating.

In the oral composition of the present invention, a middle coating may be provided between the seal coating and the coating. The oral composition of the present invention having such a middle coating can be obtained by coating a middle-coated seat-coated drug core having a seal coating and a middle coating with the coating composition of the present invention.

By providing such a middle coating over the drug core, it becomes possible increase the dissolution rate of the drug, while maintaining an unpleasant taste-masking effect.

The present middle coating is obtained by coating a drug core having a seal coating with a middle coating composition according to a known coating technique. The type of such a middle coating composition is not particularly limited, as long as it is able to enhance the disintegrating property of an over-coating that is the coating composition of the present invention. An example of such a middle coating composition is a composition comprising at least one selected from the group consisting of the above-described sugar or sugar alcohol having a solubility at 20° C. of 30 or more, low-viscosity HPMC and the like, and preferably at least one selected from the group consisting of erythritol, TC-5E (Shin-Etsu Chemical Co., Ltd.) and the like.

As a solvent that can be used to prepare the middle coating composition, water, alcohol, a mixed solvent of water and alcohol, etc. can be used.

The amount of solid ingredients contained in the middle coating composition is preferably 1% to 10% by mass, and more preferably 2% to 5% by mass, based on the mass of the drug core or orally-administered solid to be coated. The thickness of the middle coating film of the oral composition comprising the thus obtained middle coating is 10 to 80 µm, and preferably 20 to 40 µm.

The oral compositions of several embodiments of the present invention do not have a middle coating.

The oral composition of the present invention is composed of, for example, (i) a drug core/an over-coating;
(ii) a drug core/a seal coating/an over-coating; or
(iii) a drug core/a seal coating/a middle coating/an over-coating.

Preferably, it is composed of
(ii) a drug core/a seal coating/an over-coating; or
(iii) a drug core/a seal coating/a middle coating/an over-coating.

More preferably, it is composed of
(ii) a drug core/a seal coating/an over-coating.

The oral compositions of several embodiments of the present invention each have:

a drug core containing an active ingredient (preferably a tablet core, and more preferably a mini-tablet); and
over the drug core,
a carboxyvinyl polymer (e.g. Carbopol 974P (trade name)) as a first thickener,
calcium chloride as a polyvalent metal compound,
xanthan gum as a second thickener,
sucralose,
HPMC (e.g. TC-5E (trade name)),
Erythritol as sugar or sugar alcohol having a solubility at 20° C. of 30 or more, and
HPC (e.g. HPC-L (trade name)); wherein
it further has a seal coating between the drug core and the coating, but it does not have a middle coating between the seal coating and the coating.

Preferably, in the above-described coating composition, the content of the carboxyvinyl polymer in the over-coating is 3% to 20% by mass and more preferably 9% to 17% by mass (% by mass based on the total mass of all ingredients excluding a solvent; the same applies below), the content of the calcium chloride is 0.1% to 1% by mass and more preferably 0.2% to 0.7% by mass, the content of the xanthan gum is 10% to 40% by mass and more preferably 20% to 30% by mass, the content of the sucralose is 0.01% to 5% by mass and more preferably 0.5% to 1% by mass, the content of the HPMC is 5% to 35% by mass and more preferably 10% to 20% by mass, the content of the erythritol is 10% to 50% by mass and more preferably 30% to 40% by mass, and the content of the HPC is 0.1% to 15% by mass and more preferably 5% to 15% by mass.

In several embodiments of the present invention, the above-described seal coating comprises HPMC and macrogol 6000 (trade name). In this case, in the seal coating, the content of the HPMC is preferably 60% to 99% by mass and more preferably 90% to 98% by mass (% by mass based on the total mass of all ingredients excluding a solvent in the seal coating; the same applies below), and the content of the macrogol 6000 (trade name) is preferably 1% to 40% by mass and more preferably 2% to 10% by mass.

In several other embodiments of the present invention, the above-described seal coating comprises erythritol and pregelatinized starch. In this case, in the seal coating, the content of the erythritol is preferably 60% to 99% by mass and more preferably 80% to 95% by mass (% by mass based on the total mass of all ingredients excluding a solvent in the seal coating; the same applies below), and the content of the pregelatinized starch is preferably 1% to 40% by mass and more preferably 5% to 20% by mass.

In several other embodiments of the present invention, the above-described seal coating comprises HPMC and erythritol. In this case, in the seal coating, the content of the HPMC is preferably 5% to 45% by mass and more preferably 20% to 40% by mass (% by mass based on the total mass of all ingredients excluding a solvent in the seal coating; the same applies below), and the content of the erythritol is preferably 55% to 95% by mass and more preferably 60% to 80% by mass.

Preferably, in the above-described oral composition, the seal coating comprises HPMC and macrogol 6000 (trade name).

Herein, in the above-described oral composition, the content of the carboxyvinyl polymer in the over-coating is 12.7% by mass (% by mass based on the total mass of all ingredients excluding a solvent in the over-coating; the same applies below), the content of the calcium chloride is 0.5% by mass, the content of the xanthan gum is 25.3% by mass, the content of the sucralose is 0.8% by mass, the content of the HPMC is 15.2% by mass, the content of the erythritol is 35.4% by mass, and the content of the HPC is 10.1% by mass. Moreover, in the seal coating, the content of the HPMC is 95.2% by mass (% by mass based on the total mass of all ingredients excluding a solvent in the seal coating; the same applies below), and the content of the macrogol 6000 (trade name) is 4.8% by mass.

Preferably, in the above-described oral composition, the seal coating comprises HPMC and macrogol 6000 (trade name).

Herein, in the above-described oral composition, the content of the carboxyvinyl polymer in the over-coating is 9.4% by mass (% by mass based on the total mass of all ingredients excluding a solvent in the over-coating; the same applies below), the content of the calcium chloride is 0.4% by mass, the content of the xanthan gum is 26.3% by mass, the content of the sucralose is 0.9% by mass, the content of the HPMC is 15.8% by mass, the content of the erythritol is 36.8% by mass, and the content of the HPC is 10.5% by mass. Moreover, in the seal coating, the content of the HPMC is 95.2% by mass (% by mass based on the total mass of all ingredients excluding a solvent in the seal coating; the same applies below), and the content of the macrogol 6000 (trade name) is 4.8% by mass.

Preferably, in the above-described oral composition, the seal coating comprises erythritol and pregelatinized starch.

Herein, in the above-described oral composition, the content of the carboxyvinyl polymer in the over-coating is 16.7% by mass (% by mass based on the total mass of all ingredients excluding a solvent in the over-coating; the same applies below), the content of the calcium chloride is 0.6% by mass, the content of the xanthan gum is 23.4% by mass, the content of the sucralose is 0.8% by mass, the content of the HPMC is 13.9% by mass, the content of the erythritol is 33.4% by mass, and the content of the HPC is 11.1% by mass. Moreover, in the seal coating, the content of the erythritol is 90% by mass (% by mass based on the total mass of all ingredients excluding a solvent in the seal coating; the same applies below), and the content of the pregelatinized starch is 10% by mass.

Preferably, in the above-described oral composition, the seal coating comprises HPMC and erythritol.

Herein, in the above-described oral composition, the content of the carboxyvinyl polymer in the over-coating is 9.3% by mass (% by mass based on the total mass of all ingredients excluding a solvent; the same applies below), the content of the calcium chloride is 0.2% by mass, the content of the xanthan gum is 26.1% by mass, the content of the sucralose is 0.9% by mass, the content of the HPMC is 15.5% by mass, the content of the erythritol is 37.3% by mass, and the content of the HPC is 10.6% by mass. Moreover, in the seal coating, the content of the HPMC is 29.4% by mass (% by mass based on the total mass of all ingredients excluding a solvent in the seal coating; the same applies below), and the content of the erythritol is 70.6% by mass.

The drug core or orally-administered solid used in the present invention is prepared by mixing a desired drug serving as an active ingredient with pharmaceutical carriers commonly used in the technical field of pharmaceutical preparations. As such pharmaceutical carriers, carriers known in the technical field of pharmaceutical preparations can be widely used. Examples of such pharmaceutical carriers include: excipients such as lactose, saccharose, mannitol, sodium chloride, glucose, starch, calcium carbonate, kaoline, crystalline cellulose and silicate; filler such as water, ethanol, simple syrup, dextrose solution, starch solution, gelatin solution, carboxymethylcellulose, sodium carboxymethylcellulose, shellac, methylcellulose, HPMC, HPC, polyvinyl alcohol, gelatin, dextrin and Pullulan; pH adjusters such as citric acid, anhydrous citric acid, sodium citrate, sodium citrate dihydrate, anhydrous sodium monohydrogen phosphate, anhydrous sodium dihydrogen phosphate, sodium hydrogen phosphate and anhydrous sodium dihydrogen phosphate; disintegrators such as carmellose calcium, low substituted hydroxypropylcellulose, carmellose, croscarmellose sodium, partially pregelatinized starch, dry starch, sodium carboxymethyl starch, crospovidone and polysorbate 80; absorption promoters such as sodium lauryl sulfate; and lubricants such as purified talc, stearate, polyethylene glycol and colloidal silica. There may be a case in which the disintegrating property of the drug core or orally-administered solid is improved by the use of sodium carboxymethyl starch. Examples of such sodium carboxymethyl starch include Primogel (Matsutani Chemical Industry Co., Ltd.), Explotab (Kimura Sangyo Co., Ltd.), and Glycolys (Roquette Corp.).

When a coated preparation is produced using a mini-tablet and it is then administered in the form of a multi-unit, the surface layer of each tablet turns into a gel after it has been allowed to come into contact with water. At the same time, the first thickener such as a carboxyvinyl polymer and/or sodium alginate is crosslinked by polyvalent metal ions generated from the polyvalent metal compound, so that viscosity increases and a relatively hard jelly-like gel can be formed. As a result, tablets obtain a good slipping property, and good cohesiveness among tablets causes good swallowability. Moreover, since the formed gel layer suppresses the release of the drug in a short time, a higher effect of masking an unpleasant taste is exhibited.

In the oral compositions of several embodiments of the present invention, the drug core (preferably a tablet core, and more preferably a mini-tablet) comprises levofloxacin hydrate as an active ingredient, and it further comprises crystalline cellulose, sodium carboxymethyl starch, pregelatinized starch, and sodium stearyl fumarate. Preferably, in the tablet core, the content of the levofloxacin hydrate is 7% by mass to 70% by mass and preferably 35% to 70% by mass (% by mass based on the total mass of all ingredients excluding a solvent in the tablet core; the same applies below), the content of the crystalline cellulose is 1% to 20% by mass and preferably 5% to 7% by mass, the content of the sodium carboxymethyl starch is 5% to 30% by mass and preferably 15% to 20% by mass, the content of the pregelatinized starch is 0.3% to 20% by mass and preferably 1% to 5% by mass, and the content of the sodium stearyl fumarate is 0.3% to 20% by mass and preferably 1% to 5% by mass. Particularly preferably, in the tablet core, the content of the levofloxacin hydrate is 69.7% by mass (% by mass based on the total mass of all ingredients excluding a solvent in the tablet core; the same applies below), the content of the crystalline cellulose is 6.2% by mass, the content of the sodium carboxymethyl starch is 17.7% by mass, the content of the pregelatinized starch is 2.7% by mass, and the content of the sodium stearyl fumarate is 3.7% by mass.

In the oral compositions of several other embodiments of the present invention, the drug core (preferably a tablet core, and more preferably a mini-tablet) comprises valaciclovir hydrochloride as an active ingredient, and it further comprises partially pregelatinized starch, pregelatinized starch, talc, and sodium stearyl fumarate, and it further arbitrarily comprises sodium carboxymethyl starch. Preferably, in the drug core, the content of the valaciclovir hydrochloride is 7% by mass to 80% by mass and preferably 35% to 80% by mass (% by mass based on the total mass of all ingredients excluding a solvent in the tablet core; the same applies below), the content of the partially pregelatinized starch is 2% to 40% by mass and preferably 5% to 20% by mass, the content of the sodium carboxymethyl starch is 0% to 30% by mass and preferably 0% to 15% by mass, the content of the pregelatinized starch is 0.3% to 30% by mass and preferably 1% to 20% by mass, the content of the talc is 0.3% to 20% by mass and preferably 1% to 5% by mass, and the content of the sodium stearyl fumarate is 0.3% to 20% by mass and preferably 1% to 5% by mass. Particularly preferably, in the drug core, the content of the valaciclovir hydrochloride is 75.6% by mass (% by mass based on the total mass of all ingredients excluding a solvent in the tablet core; the same applies below), the content of the partially pregelatinized starch is 4.6% by mass, the content of the sodium carboxymethyl starch is 13.6% by mass, the content of the pregelatinized starch is 2.0% by mass, the content of the talc is 2.7% by mass, and the content of the sodium stearyl fumarate is 1.4% by mass. Further, particularly preferably, in the drug core, the content of the valaciclovir hydrochloride is 75.6% by mass (% by mass based on the total mass of all ingredients excluding a solvent in the tablet core; the same applies below), the content of the partially pregelatinized starch is 18.7% by mass, the content of the pregelatinized starch is 1.5% by mass, the content of the talc is 2.7% by mass, and the content of the sodium stearyl fumarate is 1.4% by mass.

The methods for producing an oral composition of the fourth and eighth aspects of the present invention are as described above.

In addition, the oral compositions of the third and seventh aspects of the present invention can be obtained by the above-described production methods. The oral composition of the third aspect of the present invention can be produced by spray-coating a drug core containing an active ingredient with a liquid that is prepared by dispersing a first thickener such as a carboxyvinyl polymer or sodium alginate (preferably, a carboxyvinyl polymer) and a second thickener such as xanthan gum, guar gum or sodium alginate (preferably, xanthan gum), with the proviso that when the first thickener is sodium alginate the second thickener is not sodium alginate, into an alcohol solution in which a polyvalent metal compound has been dissolved. Thus, as described above, the first thickener such as a carboxyvinyl polymer contained in the coating film is not substantially crosslinked by polyvalent metal ions, if the film is not allowed to come into contact with water. Moreover, the coating can be easily washed away from the oral composition of the present invention by the used alcohol solvent. On the other hand, in the case of the oral composition that has been coated using, as a solvent, a solution other than alcohol, such as an aqueous solution, since the first thickener such as a carboxyvinyl polymer contained in the coating film is substantially crosslinked by polyvalent metal ions, it is not easy to wash away the coating from the oral composition.

The easy swallowability of the oral composition according to the present invention can be specifically expressed in the form of the maximum stress that is required for the movement (rate: 8 mm/sec; up and down movement distance: 40 mm) of a probe (a ball having a diameter of 6 mm) inserted into a tube used to the filled oral composition, by the test method described in the after-mentioned Test Example 1, namely, in an evaluation using a vertically fixed silicon tube with a length of 5 cm (8×12), the bottom portion of which is sealed with absorbent cotton (25-30 mg). With regard to the oral composition of the present invention, the above-described maximum stress is preferably 41 g or less, more preferably 30 g or less, and further preferably 20 g or less. Moreover, the area under the stress-distance curve is preferably 600 g·mm or less, more preferably 400 g·mm or less, and further preferably 200 g·mm or less.

The unpleasant taste-masking effect in the present invention can be specifically expressed in the form of the concentration of the active ingredient contained in a liquid discharged from a syringe, by the test method described in the after-mentioned Test Example 2, namely, by the method comprising: placing an oral composition containing an active ingredient in a vertically fixed 2-mL plastic syringe in the same manner as that in Test Example 2; adding dropwise water heated to 37° C. to the syringe at a rate of 2 mL/min for a predetermined time, such as 30 seconds or 2 minutes; and measuring the concentration of the active ingredient contained in a liquid discharged from the port of the syringe. If the measured concentration becomes the threshold concentration or less of the unpleasant taste of the active ingredient after completion of the dropwise addition of water for 30 seconds in the aforementioned test, the oral composition of the present invention is determined to be sufficiently masked for practical use. For example, levofloxacin hydrate having a levofloxacin concentration of 1,000 μg/mL or less after completion of the dropwise addition of water for 30 seconds is considered to have a high unpleasant taste-masking effect, and thus it is preferable. Even in the case of a preparation that is administered without using water, if the concentration of the active ingredient becomes the threshold concentration or less of the unpleasant taste of the active ingredient in the aforementioned test, the preparation is determined to be sufficiently masked for practical use. In the case of levofloxacin hydrate, for example, the concentration is 100 μg/mL or less, preferably 50 μg/mL or less, and more preferably 10 μg/mL or less. In the case of valaciclovir hydrochloride, the concentration is, for example, 100 μg/mL or less, preferably 60 μg/mL or less, and more preferably 20 μg/mL or less.

The dissolution property in the present invention can be specifically expressed in the form of a dissolution rate measured 30 minutes after initiation of a test, namely, in an evaluation using Japanese Pharmacopoeia disintegration test solution 1 and the number of rotations that is 50, by Japanese Pharmacopoeia dissolution test paddle method, the test example described in the after-mentioned Test Example 3. The above-described dissolution rate of the oral composition of the present invention is preferably 60% or more, more preferably 80% or more, and further preferably 90% or more. It does not cause a substantial delay in dissolution, and it satisfies the dissolution specification of a quick-release tablet.

The type of the active ingredient contained in the drug core used in the oral composition of the present invention is not particularly limited. Taking into consideration the purpose of the present invention, a drug that is administered at a high dose for a single administration is particularly preferable. Examples of such a drug include: antibiotics such as amoxicillin, cefuroxime axetil, cephalexin, fosfomycin, ceftazidime, ampicillin, cyclacillin, lenampicillin, cefotiam hexetil, sultamicillin, vancomycin, polymyxin B, erythromycin, clarithromycin, telithromycin, azithromycin, josamycin, midecamycin, rokitamycin, roxithromycin, kanamycin, ceftibuten, chloramphenicol, cycloserine and rifabutin; synthetic antibacterial agents such as ofloxacin, enoxacin, levofloxacin, ciprofloxacin, norfloxacin, moxifloxacin, garenoxacin, lomefloxacin, nalidixic acid and linezolid; sulfa drugs such as salazosulfapyridine; antifungal agents such as voriconazole and itraconazole; antiviral agents such as aciclovir, valaciclovir, famciclovir, valganciclovir, nelfinavir, raltegravir, lamivudine, emtricitabine, ritonavir, ribavirin, abacavir, efavirenz, nelfinavir, tenofovir, disoproxil, darunavir and atazanavir; antihyperlipidemic drugs such as probucol, clofibrate, colestimide and cholestyramine; anthelminthics such as praziquantel and albendazole; antiprotozoal drugs such as tinidazole and metronidazole; agents against hepatic diseases, such as a branched chain amino acid; antidotes such as activated carbon; agents for digestive organs, such as 5-aminosalicylic acid and polycarbophil calcium; anticancer agents such as imatinib mesylate; immunosuppressive agents such as mycophenolate mofetil; and other agents such as inosine pranobex. Moreover, examples of the drug are not limited thereto. The coating composition of the present invention can also be applied to Chinese medicines, OTC medicines, and health food.

EXAMPLES

The present invention will be more specifically described in the following examples and comparative examples. However, these examples are not intended to limit the scope of the present invention.

(1) Production of Placebo Mini-Tablet (Uncoated Tablet P):

The following ingredients were weighed, mixed, and then subjected to tableting, so as to obtain 2 kg of placebo mini-tablets, each having a diameter of 3.1 mm and a thickness of 3.1 mm (approximately 25 mg/tablet; approximately 80,000 tablets).

| | |
|---|---|
| Lactose | 2.050 kg |
| Crystalline cellulose | 0.519 kg |
| Magnesium stearate | 0.026 kg |

(2) Production of Levofloxacin Hydrate Mini-Tablet and Valaciclovir Hydrochloride Mini-Tablet:

Levofloxacin hydrate or valaciclovir hydrochloride was selected as a high water-soluble model drug having a bitter taste, and levofloxacin hydrate-containing mini-tablets A to C (uncoated tablets A to C) and valaciclovir hydrochloride-containing mini-tablets D to G (uncoated tablets D to G) were then produced.

(i) Production of Levofloxacin Hydrate-Containing Mini-Tablet A (Uncoated Tablet A):

The following ingredients were weighed, and they were placed in a stirring/mixing granulator (Powrex VG-25) and were then mixed. Then, 2000 g of a 8 w/w % HPC aqueous solution was added as a binder to the mixture, followed by granulation.

| Levofloxacin hydrate | 4.100 kg |
|---|---|
| Crystalline cellulose | 0.364 kg |
| Carmellose | 0.392 kg |
| Sodium stearyl fumarate | 0.108 kg |

The granulated product was dried using a fluidized bed dryer (Powrex MP-01), and it was then sized. Thereafter, 0.087 kg of sodium stearyl fumarate was added to 4.277 kg of the obtained powders, and they were mixed and were then subjected to tableting, so as to obtain 3.612 kg of levofloxacin hydrate mini-tablets, each having a diameter of 3.1 mm and a thickness of 3.1 mm (approximately 24 mg/tablet; approximately 150,500 tablets).

(ii) Production of Levofloxacin Hydrate-Containing Mini-Tablet B (Uncoated Tablet B):

The following ingredients were weighed, and were then placed in a stirring/mixing granulator (high-speed mixer), followed by mixing. Thereafter, water was added thereto, followed by granulation.

| Levofloxacin hydrate | 205.0 g |
|---|---|
| Crystalline cellulose | 18.2 g |
| Pregelatinized starch (SWELSTAR PD-1; Asahi Kasei Corp.) | 19.6 g |
| Pregelatinized starch (SWELSTAR WB-1; Asahi Kasei Corp.) | 9.0 g |
| Sodium stearyl fumarate | 5.4 g |

The granulated product was dried using a fluidized bed dryer (Powrex MP-01), and it was then sized. Thereafter, 4.9 g of sodium stearyl fumarate was added to 239.9 g of the obtained powders, and they were mixed and were then subjected to tableting, so as to obtain approximately 220 g of levofloxacin hydrate mini-tablets, each having a diameter of 3.1 mm and a thickness of 3.1 mm (approximately 24 mg/tablet; approximately 9,200 tablets).

(iii) Production of Levofloxacin Hydrate-Containing Mini-Tablet C (Uncoated Tablet C):

<Production at 3 kg Scale>

The following ingredients were weighed, and were then placed in a stirring/mixing granulator (Powrex VG-25), followed by mixing. Thereafter, 1.93 kg of a 5 w/w % pregelatinized starch (SWELSTAR WB-1; Asahi Kasei Corporation) aqueous solution used as a binder and 1.57 kg of water were added to the mixture, followed by granulation.

| Levofloxacin hydrate | 2.471 kg |
|---|---|
| Crystalline cellulose | 0.220 kg |
| Carboxymethyl starch sodium (Primogel) | 0.627 kg |
| Sodium stearyl fumarate | 0.065 kg |

The granulated product was dried using a fluidized bed dryer (Powrex MP-01), and it was then sized. Thereafter, 0.058 kg of sodium stearyl fumarate was added to 3.095 kg of the obtained powders, and they were mixed and were then subjected to tableting, so as to obtain approximately 3 kg of levofloxacin hydrate mini-tablets, each having a diameter of 3.1 mm and a thickness of 3.1 mm (approximately 24 mg/tablet; approximately 125,000 tablets).

<Production at 50 kg Scale>

The following ingredients were weighed, and were then placed in a stirring/mixing granulator (Powrex VG-100), followed by mixing. Thereafter, 9.36 kg of a 5 w/w % pregelatinized starch (SWELSTAR WB-1; Asahi Kasei Corporation) aqueous solution used as a binder and 7.00 kg of water were added to the mixture, followed by granulation.

| Levofloxacin hydrate | 11.993 kg |
|---|---|
| Crystalline cellulose | 1.065 kg |
| Carboxymethyl starch sodium (Primogel) | 3.042 kg |
| Sodium stearyl fumarate | 0.316 kg |

The granulated product was dried using a fluidized bed dryer (Powrex WSG-30). This operation was repeated three times, and sub-batches were gathered to prepare a dry product. Thereafter, the dry product was sized, and sodium stearyl fumarate was added to the obtained powders at a ratio of 1.87 mg of the sodium stearyl fumarate to 100 mg of the obtained powders. Then, they were mixed and were then subjected to tableting, so as to obtain approximately 49 kg of levofloxacin hydrate mini-tablets, each having a diameter of 3.1 mm and a thickness of 3.1 mm.

(iv) Production of Valaciclovir Hydrochloride-Containing Mini-Tablet (Uncoated Tablet D):

The following ingredients were weighed, and were then placed in a stirring/mixing granulator (high-speed mixer), followed by mixing. Thereafter, 100 g of a 6.4 w/w % pregelatinized starch (SWELSTAR WB-1; Asahi Kasei Corporation) aqueous solution was added as a binder to the mixture, followed by granulation.

| Valaciclovir hydrochloride | 178.0 g |
|---|---|
| Crystalline cellulose | 10.2 g |
| Carboxymethyl starch sodium (Primogel) | 32.0 g |
| Sodium stearyl fumarate | 4.3 g |

The granulated product was dried using a fluidized bed dryer (Powrex MP-01), and it was then sized. Thereafter, 3.6 g of sodium stearyl fumarate was added to 197.6 g of the obtained powders, and they were mixed and were then subjected to tableting, so as to obtain approximately 177.7 g of valaciclovir hydrochloride mini-tablets, each having a diameter of 3.1 mm and a thickness of 3.1 mm (approximately 24 mg/tablet; approximately 7,400 tablets).

(v) Production of Valaciclovir Hydrochloride-Containing Mini-Tablet (Uncoated Tablet E):

The following ingredients were weighed, and were then placed in a stirring/mixing granulator (Powrex VG-25), followed by mixing. Thereafter, 1000 g of a 6 w/w % pregelatinized starch (SWELSTAR WB-1; Asahi Kasei Corporation) aqueous solution was added as a binder to the mixture, followed by granulation.

| | |
|---|---|
| Valaciclovir hydrochloride | 2224 g |
| Partially pregelatinized starch (PCS) | 136 g |
| Carboxymethyl starch sodium (Primogel) | 400 g |
| Talc | 80 g |

The granulated product was dried using a fluidized bed dryer (Powrex MP-01), and it was then sized. Thereafter, sodium stearyl fumarate was added to the obtained powders at a ratio of 1.38 mg of the sodium stearyl fumarate to 100 mg of the obtained powders, and they were mixed and were then subjected to tableting, so as to obtain approximately 2700 g of valaciclovir hydrochloride mini-tablets, each having a diameter of 3.1 mm and a thickness of 3.1 mm.

(vi) Production of Valaciclovir Hydrochloride-Containing Mini-Tablet (Uncoated Tablet F):

The following ingredients were weighed, and were then placed in a stirring/mixing granulator (Powrex VG-25), followed by mixing. Thereafter, 750 g of a 6 w/w % pregelatinized starch (SWELSTAR WB-1; Asahi Kasei Corporation) aqueous solution was added as a binder to the mixture, followed by granulation.

| | |
|---|---|
| Valaciclovir hydrochloride | 2224 g |
| Partially pregelatinized starch (PCS) | 536 g |
| Talc | 80 g |

The granulated product was dried using a fluidized bed dryer (Powrex MP-01), and it was then sized. Thereafter, sodium stearyl fumarate was added to the obtained powders at a ratio of 1.38 mg of the sodium stearyl fumarate to 100 mg of the obtained powders, and they were mixed and were then subjected to tableting, so as to obtain approximately 2600 g of valaciclovir hydrochloride mini-tablets, each having a diameter of 3.1 mm and a thickness of 3.1 mm.

(vii) Production of Valaciclovir Hydrochloride-Containing Mini-Tablet (Uncoated Tablet G):

The following ingredients were weighed, and were then placed in a stirring/mixing granulator (Powrex VG-25), followed by mixing. Thereafter, 750 g of a 6 w/w % pregelatinized starch (SWELSTAR WB-1; Asahi Kasei Corporation) aqueous solution was added as a binder to the mixture, followed by granulation.

| | |
|---|---|
| Valaciclovir hydrochloride | 2224 g |
| Partially pregelatinized starch | 551 g |
| Talc | 80 g |

The granulated product was dried using a fluidized bed dryer (Powrex MP-01), and it was then sized. Thereafter, sodium stearyl fumarate was added to the obtained powders at a ratio of 1.38 mg of the sodium stearyl fumarate to 100 mg of the obtained powders, and they were mixed and were then subjected to tableting, so as to obtain approximately 2700 g of valaciclovir hydrochloride mini-tablets, each having a diameter of 3.1 mm and a thickness of 3.1 mm.

The compositions of the uncoated tablets A-G (wherein each numeral value indicates the amount of each gradient per 500 mg of the active ingredient) are shown in Table 1.

TABLE 1

| Ingredient | Uncoated tablet A | Uncoated tablet B | Uncoated tablet C | Uncoated tablet D | Uncoated tablet E | Uncoated tablet F | Uncoated tablet G |
|---|---|---|---|---|---|---|---|
| Levofloxacin hydrate | 512.5 | 512.5 | 512.5 | | | | |
| Valaciclovir hydrochloride | | | | 556 | 556 | 556 | 556 |
| Crystalline cellulose | 45.5 | 45.5 | 45.5 | 32 | | | |
| Partially pregelatinized starch (PCS) | | | | | 34 | 134 | 137.75 |
| Carmellose | 49 | | | | | | |
| Pregelatinized starch (SWELSTAR PD-1) | | 130 | | | | | |
| Carboxymethyl starch sodium (Primogel) | | | 130 | 100 | 100 | | |
| HPC-L | 20 | | | | | | |
| Pregelatinized starch (SWELSTAR WB-1) | | 20 | 20 | 20 | 15 | 11.25 | 11.25 |
| Talc | | | | | 20 | 20 | 20 |
| Sodium stearyl fumarate | 27 | 27 | 27 | 27 | 10 | 10 | 10 |

Examples 1 and 2

Concentrated glycerin was mixed into ethanol, and HPC (HPC-L; Nippon Soda Co., Ltd.; indicated viscosity: 6 to 10 mPa·s) was then added to and dissolved in the solution. Thereafter, HPMC (TC-5E; Shin-Etsu Chemical Co., Ltd.; indicated viscosity: 3 mPa·s) and a carboxyvinyl polymer (Carbopol 971P; Lubrizol Advanced Material Inc.; indicated viscosity: 6420 mPa·s) were successively added to the mixed solution, and they were then uniformly dispersed therein. Thereafter, erythritol (Mitsubishi Shoji Foodtech Co., Ltd.) and xanthan gum (Keltrol CG-T; Sansho Co., Ltd.; indicated viscosity: 1555 mPa·s) were micronized using a jet mill (Seishin Enterprise Co., Ltd.; SJ-3), and then, they were successively added to the solution, so that they were uniformly dispersed therein. Finally, a calcium chloride dihydrate dissolved in ethanol was added to the solution, and they were uniformly dispersed therein, so as to prepare a coating solution. This coating solution was applied by spray-coating onto the above-described uncoated tablet A, using a coater (Powrex Dria-Coater 200), so as to obtain a coated mini-tablet (coating rate: approximately 10% at a mass ratio to the coated mini-tablet). 140 g of uncoated tablets (approximately 5,833 tablets) were coated by a single coating operation.

Moreover, as Examples 1-P and 2-P, coated mini-tablets (140 g of uncoated tablets; approximately 5,833 tablets) were obtained by the same preparation methods as those of Examples 1 and 2, respectively, with the exception that uncoated tablets P were used instead of the uncoated t ablets A.

Example 3

Coated mini-tablets were obtained by a preparation method equivalent to that of Example 1, with the exception that HPC-L was not added in the method for preparing a coating solution of Example 1.

Example 4

Coated mini-tablets were obtained by a preparation method equivalent to that of Example 1, with the exception that Carbopol 974P (Lubrizol Advance Material Inc.; indicated viscosity: 32850 mPa·s) was used instead of Carbopol 971P in the method for preparing a coating solution of Example 2.

Example 1-1

Coated mini-tablets were obtained by a preparation method equivalent to that of Example 1, with the exception that mannitol (mannit P; Mitsubishi Shoji Foodtech Co., Ltd.) micronized with a jet mill was used instead of erythritol in the method for preparing a coating solution of Example 1.

Example 1-2

Coated mini-tablets were obtained by a preparation method equivalent to that of Example 1, with the exception that HPMC was not used in the method for preparing a coating solution of Example 1.

Example 1-3

Coated mini-tablets were obtained by a preparation method equivalent to that of Example 1, with the exception that HPMC was not used and the amount of erythritol was increased in the method for preparing a coating solution of Example 1.

Example 1-4

Coated mini-tablets were obtained by a preparation method equivalent to that of Example 1, with the exception that the amount of Carbopol 971P was increased and the amount of erythritol was decreased in the method for preparing a coating solution of Example 1.

Example 1-5

Coated mini-tablets were obtained by a preparation method equivalent to that of Example 1, with the exception that erythritol was not used and the amount of HPMC was increased in the method for preparing a coating solution of Example 1.

Example 2-1

Coated mini-tablets were obtained by a preparation method equivalent to that of Example 1, with the exception that Carbopol 971P was not used in the method for preparing a coating solution of Example 1.

Example 2-2

Coated mini-tablets were obtained by a preparation method equivalent to that of Example 1, with the exception that xanthan gum was not used in the method for preparing a coating solution of Example 1.

Comparative Example 1

As Comparative Example 1, uncoated tablets A obtained as a result of the above-described production of levofloxacin hydrate mini-tablets were used.

Comparative Example 2

Ordinary film coated mini-tablets were prepared for the purpose of light-shielding or the masking of a bitter taste. HPMC and macrogol 6000 (Wako Pure Chemical Industries, Ltd.) were dissolved in water, and thereafter, talc (Matsumura Sangyo Co.) and titanium oxide (Freund) were uniformly dispersed therein, so as to prepare a coating solution. Thereafter, the above-described uncoated tablets P or uncoated tablets A were coated with this coating solution, using a coater (Powrex Dria-Coater 200), so as to obtain coated mini-tablets (coating rate: approximately 10% at a mass ratio to the coated mini-tablets).

Comparative Example 3

Coated mini-tablets were obtained by a preparation method equivalent to that of Example 1, with the exception that neither HPMC nor calcium chloride dihydrate was used and mannitol (mannit P; Mitsubishi Shoji Foodtech Co., Ltd.) crushed with a jet mill was used instead of erythritol micronized with a jet mill in the method for preparing a coating solution of Example 1.

The composition of the coating solution of each of Examples 1 to 4 and 1-1 to 2-2, and Comparative Examples 2 and 3, is shown in Table 2 (parts).

TABLE 2

| Ingredient | Example | | | | | | | | | | | Comp. Ex. | |
| --- | --- | --- | --- | --- | --- | --- | --- | --- | --- | --- | --- | --- | --- |
| | 1 | 2 | 3 | 4 | 1-1 | 1-2 | 1-3 | 1-4 | 1-5 | 2-1 | 2-2 | 2 | 3 |
| Uncoated tablet | A | A | A | A | A | A | A | A | A | A | A | A | A |
| Seal coating | No | No | No | No | No | No | No | No | No | No | No | No | No |
| Carbopol 974P | | | | 1.00 | | | | | | | | | |
| Carbopol 971P | 1.50 | 0.50 | 1.50 | | 1.50 | 1.50 | 1.50 | 2.00 | 1.50 | | 1.50 | | 1.50 |
| Xanthan gum (jet mill crushing) Particle diameter ($D_{50}$): 13.3 μm | 3.00 | 3.00 | 3.00 | 3.00 | 3.00 | 3.00 | 3.00 | 3.00 | 3.00 | 3.00 | | | 3.00 |

TABLE 2-continued

| Ingredient | Example 1 | 2 | 3 | 4 | 1-1 | 1-2 | 1-3 | 1-4 | 1-5 | 2-1 | 2-2 | Comp. Ex. 2 | 3 |
|---|---|---|---|---|---|---|---|---|---|---|---|---|---|
| HPC-L | 1.20 | 1.20 | | | 1.20 | 1.20 | 1.20 | 1.20 | 1.20 | 1.20 | 1.20 | | 1.20 |
| HPMC | 1.80 | 1.80 | 3.00 | 3.00 | 1.80 | | | 1.80 | 4.20 | 1.80 | 1.80 | 4.62 | |
| Marmit (jet mill crushing) Particle diameter ($D_{50}$): 5.7 µm | | | | | 4.20 | | | | | | | | 4.20 |
| Erythritol (jet mill crushing) Particle diameter ($D_{50}$): 3.8 µm | 4.20 | 5.30 | 4.20 | 4.75 | | 4.20 | 6.00 | 3.70 | | 4.20 | 4.20 | | |
| Calcium chloride dihydrate | 0.15 | 0.05 | 0.15 | 0.10 | 0.15 | 0.15 | 0.15 | 0.15 | 0.15 | | 0.15 | | |
| Macrogol 6000 | | | | | | | | | | | | 0.92 | |
| Talc | | | | | | | | | | | | 1.38 | |
| Titanium oxide | | | | | | | | | | | | 3.08 | |
| Concentrated glycerin | 0.60 | 0.60 | 0.60 | 0.60 | 0.60 | 0.60 | 0.60 | 0.60 | 0.60 | 0.60 | 0.60 | | 0.60 |
| Ethanol | 80.00 | 80.00 | 80.00 | 80.00 | 80.00 | 80.00 | 80.00 | 80.00 | 81.00 | 80.00 | 80.00 | | 81.00 |
| Water | | | | | | | | | | | | 90.00 | |

Example 5

140 g of the above-described uncoated tablets C were spray-coated with a coating solution (seal coating solution I) prepared by dissolving macrogol 6000 in water and then dissolving HPMC (TC-5R; Shin-Etsu Chemical Co., Ltd.) therein, using a coater (Powrex Dria Coater 200), so as to obtain seal-coated mini-tablets (coating rate: approximately 4% at a mass ratio to the seal-coated mini-tablets). Subsequently, HPC (HPC-L; Nippon Soda Co., Ltd.; indicated viscosity: 6 to 10 mPa·s) was added to and dissolved in ethanol. Thereafter, HPMC (TC-5E; Shin-Etsu Chemical Co., Ltd.) and a carboxyvinyl polymer (Carbopol 971P; Lubrizol Advanced Material Inc.; indicated viscosity: 6420 mPa·s) were successively added to the solution, and they were uniformly dispersed therein. Thereafter, erythritol (Mitsubishi Shoji Foodtech Co., Ltd.) and xanthan gum (Keltrol CG-T; Sansho Co., Ltd.; indicated viscosity: 1555 mPa·s) were micronized with a jet mill (Seishin Enterprise Co., Ltd.; SJ-3), and thereafter, they were successively added to the solution and were then uniformly dispersed therein. Finally, a solution prepared by dissolving calcium chloride dihydrate in ethanol was added to the solution, and it was uniformly dispersed therein, so as to prepare an over-coating solution. The above-described seal-coated mini-tablets were spray-coated with this over-coating solution, using a coater (Powrex Dria Coater 200), so as to obtain coated mini-tablets (coating rate: approximately 8% at a mass ratio to the coated mini-tablets).

Example 6

Coated mini-tablets were obtained by a preparation method equivalent to that of Example 5, with the exception that maltitol (Amalty MR-100; Mitsubishi Shoji Foodtech Co., Ltd.) micronized with a jet mill was used instead of erythritol in the method for preparing an over-coating solution of Example 5.

Example 7

Coated mini-tablets were obtained by a preparation method equivalent to that of Example 5, with the exception that trehalose (trehalose S; Asahi Kasei Chemicals Corporation) micronized with a jet mill was used instead of erythritol in the method for preparing an over-coating solution of Example 5.

Example 8

Coated mini-tablets were obtained by a preparation method equivalent to that of Example 5, with the exception that guar gum (guar gum RG-100; MRC Polysaccharide Co., Ltd.; indicated viscosity: 1100 mPa·s) micronized with a jet mill was used instead of xanthan gum in the method for preparing an over-coating solution of Example 5.

Example 9-1

Coated mini-tablets were obtained by a preparation method equivalent to that of Example 5, with the exception that sodium alginate (Kimica Algin 1-8; KIMICA Corporation) micronized with a jet mill was used instead of xanthan gum in the method for preparing an over-coating solution of Example 5.

Example 9-2

Coated mini-tablets were obtained by a preparation method equivalent to that of Example 5, with the exception that sodium alginate (Kimica Algin 1-8; KIMICA Corporation) micronized with a jet mill was used instead of the carboxyvinyl polymer in the method for preparing an over-coating solution of Example 5.

Example 10

Coated mini-tablets were obtained by a preparation method equivalent to that of Example 5, with the exception that uncoated tablets A were used instead of uncoated tablets C in Example 5.

Example 11

Coated mini-tablets were obtained by a preparation method equivalent to that of Example 5, with the exception that uncoated tablets B were used instead of uncoated tablets C in Example 5.

Example 12

Approximately 2 kg of the same uncoated tablets C as those used in Example 5 were spray-coated with a seal coating solution having the same composition as that of Example 5 (seal coating solution I), using a coater (Powrex Coater 7), so as to obtain seal-coated mini-tablets (coating rate: approximately 4% at a mass ratio to the seal-coated mini-tablets). Subsequently, sucralose and HPC (HPC-L; Nippon Soda Co., Ltd.) were added to and dissolved in ethanol. Thereafter, HPMC (TC-5E; Shin-Etsu Chemical Co., Ltd.) and a carboxyvinyl polymer (Carbopol 971P; Lubrizol Advanced Material Inc.; indicated viscosity: 6420 mPa·s) were successively added to the solution, and they were uniformly dispersed therein. Thereafter, erythritol (Mitsubishi Shoji Foodtech Co., Ltd.) and xanthan gum (Keltrol CG-T; Sansho Co., Ltd.; indicated viscosity: 1555 mPa·s) were micronized with a jet mill (Seishin Enterprise Co., Ltd.; SJ-3), and thereafter, they were successively added to the solution and were then uniformly dispersed therein. Finally, a solution prepared by dissolving calcium chloride dihydrate in ethanol was added to the solution, and it was uniformly dispersed therein, so as to prepare an over-coating solution. The above-described seal-coated mini-tablets were spray-coated with this over-coating solution, using a coater (Powrex Coater 7), so as to obtain coated mini-tablets (coating rate: approximately 4.5% at a mass ratio to the coated mini-tablets).

Example 13

Approximately 50 kg of the same uncoated tablets C as those used in Example 12 were spray-coated with a seal coating solution having the same composition as that of Example 12 (seal coating solution I), using a coater (Powrex Coater 150), so as to obtain seal-coated mini-tablets (coating rate: approximately 4% at a mass ratio to the seal-coated mini-tablets). Subsequently, the above-described seal-coated mini-tablets were spray-coated with an over-coating solution having the same composition as that of Example 12, using a coater (Powrex Coater 150), so as to obtain coated mini-tablets (coating rate: approximately 4.5% at a mass ratio to the coated mini-tablets).

Comparative Example 4

The above-described uncoated tablets C were used as Comparative Example 4.

Comparative Example 5

The seal-coated mini-tablets prepared in Example 5 were used as Comparative Example 5.

Comparative Example 6

The uncoated tablets D were used as Comparative Example 6.

The uncoated tablets and the compositions (parts) of seal coating solutions and over-coating solutions used in Examples 5-8, 9-1, 9-2 and 10 to 13, and Comparative Examples 4 and 5 are shown in Table 3. In addition, the compositions (parts) of seal coating solutions and middle coating solutions used for coating in Examples 5-23 and Comparative Examples 5 and 6 are shown in Table 4. The coating rate (%) in Table 3 was obtained as follows.

Coating rate (%) of seal coating=(Mass of 100 tablets after seal coating−mass of 100 uncoated tablets)/Mass of 100 tablets after seal coating× 100

Coating rate (%) of over-coating=(Mass of 100 tablets after over-coating−mass of 100 uncoated tablets)/Mass of 100 tablets after over-coating× 100

(It is to be noted that the mass of each tablet is indicated by a moisture correction value.)

TABLE 3

| Constitution | Ingredient | Example 5 | 6 | 7 | 8 | 9-1 | 9-2 | 10 | 11 | 12 | 13 | Comparative Example 4 | 5 |
|---|---|---|---|---|---|---|---|---|---|---|---|---|---|
| Uncoated tablet | Composition | C | C | C | C | C | C | A | B | C | C | C | C |
| Seal coating | Composition | I | I | I | I | I | I | I | I | I | I | No | I |
|  | Coating rate (%) |  |  |  |  | Approx. 4 |  |  |  |  |  |  | Approx. 4 |
| Over-coating | Carbopol 974P | 1.05 | 1.05 | 1.05 | 1.05 | 1.05 |  | 1.05 | 1.05 | 1.05 | 0.75 | Over-coating: No | Over-coating: No |
|  | Xanthan gum (jet mill crushing) | 2.10 | 2.10 | 2.10 |  |  | 2.10 | 2.10 | 2.10 | 2.10 | 2.10 |  |  |
|  | Guar gum (jet mill crushing) |  |  |  | 2.10 |  |  |  |  |  |  |  |  |
|  | Sodium alginate (jet mill crushing) |  |  |  |  | 2.10 | 1.05 |  |  |  |  |  |  |
|  | HPC-L | 0.84 | 0.84 | 0.84 | 0.84 | 0.84 | 0.84 | 0.84 | 0.84 | 0.84 | 0.84 |  |  |
|  | HPMC | 1.26 | 1.26 | 1.26 | 1.26 | 1.26 | 1.26 | 1.26 | 1.26 | 1.26 | 1.26 |  |  |
|  | Erythritol (jet mill crushing) | 2.94 |  |  | 2.94 | 2.94 | 2.94 | 2.94 | 2.94 | 2.94 | 2.94 |  |  |
|  | Maltitol (jet mill crushing) |  | 2.94 |  |  |  |  |  |  |  |  |  |  |
|  | Trehalose (jet mill crushing) |  |  | 2.94 |  |  |  |  |  |  |  |  |  |
|  | Calcium chloride | 0.04 | 0.04 | 0.04 | 0.04 | 0.04 | 0.04 | 0.04 | 0.04 | 0.04 | 0.03 |  |  |
|  | Sucralose |  |  |  |  |  |  |  |  | 0.07 | 0.07 |  |  |
|  | Ethanol | 49.00 | 49.00 | 49.00 | 49.00 | 49.00 | 49.00 | 49.00 | 49.00 | 49.00 | 49.00 |  |  |
|  | Coating rate (%) |  |  |  | Approx. 8 |  |  |  |  | 4.5 | 4.5 |  |  |

TABLE 4

| Constitution | Ingredient | I | II | III | IV | V | VI | VII |
|---|---|---|---|---|---|---|---|---|
| Seal coating | HPMC (TC-5R; viscosity: 6 mPa·s) | 4 | 4 | 4 | | | | 4 |
| | HPMC (TC-5E; viscosity: 3 mPa·s) | | | | | | 1.25 | |
| | Pregelatinized starch (SWELSTAR WB-1) | | | | 1.1 | 0.55 | | |
| | Erythritol | | | | 4.4 | 4.95 | 3 | |
| | Macrogol 6000 | 0.2 | 0.2 | 0.2 | | | | |
| | Talc | | | 0.5 | | | | 2 |
| | Light anhydrous silicic acid | | 1 | | | | | |
| | Water | 50 | 50 | 50 | 50 | 50 | 35 | 35 |
| | Ethanol | | | | | | 15 | 15 |
| Middle coating | Erythritol | | | | | | | 8 |
| | Water | | | | | | | 50 |

Example 14

Coated mini-tablets were obtained by a preparation method equivalent to that of Example 5, with the exception that uncoated tablets D were used instead of uncoated tablets C in Example 5. The coating rate of the over-coating was set at 5.0% at a mass ratio to the coated mini-tablets.

Example 15

Approximately 2 kg of the uncoated tablets E were spray-coated with a coating solution prepared by dissolving erythritol in water and then dissolving pregelatinized starch (SWELSTAR WB-1; Asahi Kasei Corp.) therein, using a coater (Powrex Coater 7), so as to obtain seal-coated mini-tablets (seal coating solution IV; coating rate: approximately 4.9% at a mass ratio to the seal-coated mini-tablets). Subsequently, sucralose and HPC (HPC-L; Nippon Soda Co., Ltd.) were added to and dissolved in ethanol. Thereafter, HPMC (TC-5E; Shin-Etsu Chemical Co., Ltd.) and a carboxyvinyl polymer (Carbopol 971P; Lubrizol Advanced Material Inc.; indicated viscosity: 6420 mPa·s) were successively added to the solution, and they were uniformly dispersed therein. Thereafter, erythritol (Mitsubishi Shoji Foodtech Co., Ltd.) and xanthan gum (Keltrol CG-T; Sansho Co., Ltd.; indicated viscosity: 1555 mPa·s) were micronized with a jet mill (Seishin Enterprise Co., Ltd.; SJ-3), and thereafter, they were successively added to the solution and were then uniformly dispersed therein. Finally, a solution prepared by dissolving calcium chloride dihydrate in ethanol was added to the solution, and it was uniformly dispersed therein, so as to prepare an over-coating solution. The above-described seal-coated mini-tablets were spray-coated with this over-coating solution, using a coater (Powrex Coater 7), so as to obtain coated mini-tablets (coating rate: approximately 5% at a mass ratio to the coated mini-tablets).

Example 16

Coated mini-tablets were obtained by a preparation method equivalent to that of Example 15, with the exception that the amount of the pregelatinized starch was decreased whereas the amount of the erythritol was increased (the seal coating solution V), in the method for preparing a seal coating solution of Example 15.

Example 17

Coated mini-tablets were obtained by a preparation method equivalent to that of Example 15, with the exceptions that the seal coating solution I was used instead of the seal coating solution V in the method for preparing a seal coating solution of Example 15, and that the additive amounts of a carboxyvinyl polymer, calcium chloride and HPC-L were decreased, and sucralose was added in the method for preparing an over-coating solution.

Example 18

Coated mini-tablets were obtained by a preparation method equivalent to that of Example 17, with the exceptions that light anhydrous silicic acid was added in the method for preparing a seal coating solution of Example 17 (the seal coating solution II), and that the coating rate of the over-coating was reduced to 3.0% at a mass ratio to the coated mini-tablets.

Example 19

Coated mini-tablets were obtained by a preparation method equivalent to that of Example 18, with the exceptions that uncoated tablets F were used instead of the uncoated tablets E in Example 18, and that talc was used instead of light anhydrous silicic acid in the method for preparing a seal coating solution.

Example 20

Coated tablets were obtained by a preparation method equivalent to that of Example 18, with the exceptions that uncoated tablets F were used instead of the uncoated tablets E in Example 18, that the coating rate of the seal coating was increased, and that the additive amount of a carboxyvinyl polymer and the coating rate of the over-coating were increased in the method for preparing an over-coating solution.

Example 21

Coated mini-tablets were obtained by a preparation method equivalent to that of Example 18, with the exceptions that uncoated tablets G were used instead of the uncoated tablets F in Example 18, and that the HPMC TC-5R was replaced with HPMC TC-5E having a lower viscosity and erythritol was added instead of macrogol 6000 and light anhydrous silicic acid, and further ethanol was added as a solvent (seal coating solution VI), in the method for preparing a seal coating solution.

Example 22

Coated tablets were obtained by a preparation method equivalent to that of Example 21, with the exceptions that the coating rate of the seal coating was increased in Example 21, and that the additive amount of a carboxyvinyl polymer and the coating rate of the over-coating were increased in the method for preparing an over-coating solution.

Example 23

Approximately 5 kg of the above-described uncoated tablets G were spray-coated with a coating solution (seal coating solution VIII) prepared by dissolving HPMC (TC-5R; Shin-Etsu Chemical Co., Ltd.) in a mixed solution of water and ethanol (35:15) and then dispersing talc therein, using a coater (Powrex Coater 7), so as to obtain seal-coated mini-tablets (coating rate: 3.0% at a mass ratio to the seal-coated mini-tablets). Subsequently, the seal-coated mini-tablets were spray-coated with a coating solution (middle coating solution VIII) prepared by dissolving erythritol in water, using a coater (Powrex Coater 7), so as to obtain middle-coated mini-tablets (coating rate: 3.0% at a mass ratio to the middle-coated mini-tablets). Sucralose and HPC (HPC-L; Nippon Soda Co., Ltd.) were added to and dissolved in ethanol. Thereafter, HPMC (TC-5E; Shin-Etsu Chemical Co., Ltd.) and a carboxyvinyl polymer (Carbopol 971P; Lubrizol Advanced Material Inc.; indicated viscosity: 6420 mPa·s) were successively added to the solution, and they were uniformly dispersed therein. Thereafter, erythritol (Mitsubishi Shoji Foodtech Co., Ltd.) and xanthan gum (Keltrol CG-T; Sansho Co., Ltd.; indicated viscosity: 1555 mPa·s) were micronized with a jet mill (Seishin Enterprise Co., Ltd.; SJ-3), and thereafter, they were successively added to the solution and were then uniformly dispersed therein. Finally, a solution prepared by dissolving calcium chloride dihydrate in ethanol was added to the solution, and it was uniformly dispersed therein, so as to prepare an over-coating solution. The above-described middle-coated mini-tablets were spray-coated with this over-coating solution, using a coater (Powrex Coater 7), so as to obtain coated mini-tablets (coating rate: 4.0% at a mass ratio to the coated mini-tablets).

Comparative Example 6

The above-described uncoated tablets D were used as Comparative Example 6.

Table 5 shows the uncoated tablets and the compositions (parts) of seal coating and over-coating solutions used in Examples 14 to 23 and Comparative Example 6. In addition, the coating rate (%) in Table 5 was obtained as follows.

Coating rate (%) of seal coating=(Mass of 100 tablets after seal coating–mass of 100 uncoated tablets)/Mass of 100 tablets after seal coating×100

Coating rate (%) of middle coating=(Mass of 100 tablets after middle coating–mass of 100 seal-coated tablets)/Mass of 100 tablets after middle coating×100

Coating rate (%) of over-coating=(Mass of 100 tablets after over-coating–mass of 100 seal-coated or middle coated tablets)/Mass of 100 tablets after over-coating×100

(It is to be noted that the mass of each tablet is indicated by a moisture correction value.)

TABLE 5

| Constitution | Ingredient | Example 14 | 15 | 16 | 17 | 18 | 19 | 20 | 21 | 22 | 23 | Comparative Example 6 |
|---|---|---|---|---|---|---|---|---|---|---|---|---|
| Uncoated tablet | Composition | D | E | E | E | E | F | F | G | G | G | D |
| Seal coating | Composition | I | IV | V | I | II | III | II | VI | VI | VII* | No |
|  | Coating rate (%) | 4.2 | 4.9 | 4.5 | 4.0 | 4.0 | 4.0 | 3.0 | 4.0 | 5.0 | 3.0 |  |
| Over-coating | Carbopol 974P | 1.05 | 1.50 | 1.50 | 0.75 | 0.75 | 0.75 | 1.25 | 0.75 | 1.50 | 0.75 | Over-coating: No |
|  | Xanthan gum (jet mill crushing) | 2.10 | 2.10 | 2.10 | 2.10 | 2.10 | 2.10 | 2.10 | 2.10 | 2.10 | 2.10 |  |
|  | HPC-L | 0.84 | 1.00 | 1.00 | 0.84 | 0.84 | 0.84 | 0.85 | 0.85 | 0.85 | 0.85 |  |
|  | HPMC (TC-5E; viscosity: 3 mPa · s) | 1.26 | 1.25 | 1.25 | 1.26 | 1.25 | 1.25 | 1.25 | 1.25 | 1.25 | 1.25 |  |
|  | Erythritol (jet mill crushing) | 2.94 | 3.00 | 3.00 | 2.94 | 2.94 | 2.94 | 3.00 | 3.00 | 3.00 | 3.00 |  |
|  | Calcium chloride | 0.04 | 0.05 | 0.05 | 0.02 | 0.02 | 0.02 | 0.03 | 0.02 | 0.05 | 0.02 |  |
|  | Sucralose |  | 0.07 | 0.07 | 0.07 | 0.07 | 0.07 | 0.07 | 0.07 | 0.07 | 0.07 |  |
|  | Ethanol | 49.00 | 49.00 | 49.00 | 49.00 | 49.00 | 49.00 | 49.00 | 49.00 | 49.00 | 49.00 |  |
|  | Coating rate (%) | 5.0 | 4.9 | 4.8 | 5.0 | 3.0 | 3.0 | 4.0 | 3.0 | 5.0 | 4.0 |  |

*Coating rate of middle coating: 4.0%

Reference Example 1

A solution was prepared according to liquid A described in Production Example 1 of Patent Literature 4. Specifically, 3.0 g of hydrolyzed polyvinyl alcohol (Wako Pure Chemical Industries, Ltd.) was slowly added to 55.0 g of purified water, while stirring. Thereafter, while heating to 70° C., the obtained mixture was stirred for approximately 1 hour, so that it was completely dissolved in the purified water. Likewise, 1.0 g of Carbopol 974P was slowly added to 45.0 g of purified water, while stirring, and the obtained mixture was then stirred for approximately 30 minutes, so that it was completely dissolved in the purified water. The thus obtained two types of solutions were gathered, and the mixed solution was then fully stirred. Since the solution obtained at this time point did not contain calcium chloride, it had extremely high viscosity although it was not crosslinked by polyacrylic acid. Thus, the solution could not used for spray-coating using the spray-coater described in Example 1. Accordingly, it was assumed that it would be difficult to carry out spray-coating, using a solution prepared by adding calcium chloride to the aforementioned solution so that the resultant solution would be crosslinked by polyacrylic acid with the action of calcium ions generated as a result of the electrolytic dissociation of the added calcium chloride.

Reference Example 2

An inner coating solution was prepared in the same manner as that of Reference Example 1, with the exception that 0.33 g of glycerin was added to the prescription of Reference Example 1 and the total amount of purified water added was set at 250 g. At the same time, while stirring, 1.0 g of glycerin, 3.5 g of polyvinylpyrrolidone (PVP K-90, ISP Japan Ltd.), 0.5 g of calcium chloride and 0.5 g of xanthan gum (Keltrol CG-T; Sansho Co., Ltd.; indicated viscosity: 1555 mPa·s) were slowly added to 170 g of purified water. Thereafter, while heating to 70° C., the obtained mixture was stirred for approximately 30 minutes, so that the aforementioned substances were completely dissolved in the purified water, thereby preparing an outer coating solution.

The above-described uncoated tablets P were spray-coated with the inner coating solution, using a coater (Powrex Dria Coater 200), and they were then dried. Thereafter, the tablets were also spray-coated with the outer coating solution in the same manner as described above, so as to obtain coated mini-tablets. Even though coating operations were carried out twice, the mass ratio of the inner and outer coating films to the mini-tablets remained at approximately 4.3%.

Test Example 1 (Evaluation of Slipping Property)

A silicon tube (8×12; inner diameter: 8 mm, outer diameter: 12 mm) was cut into a length of 5 cm, and it was then vertically fixed on an aluminum block, using an adhesive tape. The bottom portion thereof was sealed with absorbent cotton (25 to 30 mg), and 20 mini-tablets were then placed therein from the upper portion, followed by tapping. Using a syringe, 5 mL of water was supplied into the silicon tube. Immediately after the water had been discharged, a probe (a ball-type probe with a diameter of 6 mm) set into a texture analyzer (TA-XT-Plus) manufactured by Stable Micro Systems was inserted into the tube, and it was then moved 40 mm from the top to the bottom at a rate of 8 mm/sec. The stress required at that time was measured.

Test Example 2 (Evaluation of Bitter Taste-Masking)

A 2.5-mL plastic syringe was vertically placed, and it was then filled with approximately 27 to 30 coated mini-tablets containing levofloxacin hydrate or valaciclovir hydrochloride (500 mg of levofloxacin or valaciclovir). Thereafter, from above, water heated to 37° C. was added dropwise to the syringe at a flow rate of 2 mL/min for 30 seconds or 2 minutes. A liquid discharged from the port of the syringe was gathered, and the concentration of levofloxacin hydrate or valaciclovir hydrochloride contained therein was then measured.

Test Example 3 (Evaluation of Dissolution Property)

Approximately 27 to 30 coated mini-tablets containing levofloxacin hydrate or valaciclovir hydrochloride (500 mg of levofloxacin or valaciclovir) were tested according to the Japanese Pharmacopoeia dissolution test paddle method (test solution: Japanese Pharmacopoeia disintegration test solution 1; the number of rotations: 50). The dissolution rate at 30 minutes after initiation of the test was measured. The test results are shown in Tables 6 to 8.

TABLE 6

| Test Example | Evaluation item | Example 1 | 2 | 3 | 4 | 1-1 | 1-2 | 1-3 |
|---|---|---|---|---|---|---|---|---|
| 1 | Maximum stress (g) | 10.3 | 29.3 | 26.3 | 36.9 | 28.9 | 23.0 | 24.6 |
|   | Area under the stress-distance curve (g · mm) | 133 | 472 | 386 | 516 | 347 | 323 | 297 |
| 2 | Concentration of liquid discharged for 2 minutes (μg/mL) | 0.652 | 0.831 | 2.33 | 0.737 | 0.579 | 0.249 | 0.577 |
| 3 | Dissolution rate (%) for 30 minutes Test solution: pH 1.2 | 86.1 | 88.7 | 92.8 | 82.2 | 42.4 | 47.3 | 52.1 |

| Test Example | Evaluation item | Example 1-4 | 1-5 | 2-1 | 2-2 | Comparative Example 1 | 2 | 3 |
|---|---|---|---|---|---|---|---|---|
| 1 | Maximum stress (g) | 40.6 | 29.8 | 46.0 | 85.3 | 1135 | 125.8 | 132.5 |
|   | Area under the stress-distance curve (g · mm) | 516 | 501 | 801 | 1624 | 20806 | 2779 | 974 |
| 2 | Concentration of liquid discharged for 2 minutes (μg/mL) | 0.477 | 0.764 | 3.69 | 4.89 | 10033 | 677 | 0.148 |
| 3 | Dissolution rate (%) for 30 minutes Test solution: pH 1.2 | 66.2 | 30.0 | 81.2 | 74.0 | 102.0 | 97.8 | 61.5 |

TABLE 7

| Test Example | Evaluation item | Example 5 | 6 | 7 | 8 | 9-1 | 9-2 | 10 | 11 | 12 | 13 | Comparative Example 4 | 5 |
|---|---|---|---|---|---|---|---|---|---|---|---|---|---|
| 1 | Maximum stress (g) | 17.3 | 22.5 | 20.4 | 25.2 | 24.0 | 31.1 | 17.1 | 19.4 | ○ | ○ | — | — |
|  | Area under the stress-distance curve (g · mm) | 164 | 220 | 326 | 399 | 408 | 426 | 308 | 306 | ○ | ○ | — | — |
| 2 | Concentration of liquid discharged for 30 seconds (μg/mL) | 17.4 | 18.9 | 47.9 | 40.6 | 42.1 | 29.6 | 23.2 | 25.3 | ○ | ○ | 2494.3 | 124.7 |
| 3 | Dissolution rate (%) for 30 minutes Test solution: pH 1.2 | 103.5 | 104.5 | 105.4 | 105.5 | 105.0 | 106.0 | 106.4 | 110.5 | ◎ | ◎ | — | — |

TABLE 8

| Test Example | Evaluation item | Example 14 | 15 | 16 | 17 | 18 | 19 | 20 | 21 | 22 | 23 | Comp. Ex. 6 |
|---|---|---|---|---|---|---|---|---|---|---|---|---|
| 1 | Maximum stress (g) | ○ | ○ | ○ | ○ | ○ | ○ | ○ | ○ | ○ | ○ | — |
|  | Area under the stress-distance curve (g · mm) | ○ | ○ | ○ | ○ | ○ | ○ | ○ | ○ | ○ | ○ | — |
| 2 | Concentration of liquid discharged for 30 seconds (μg/mL) | ○ | ○ | ○ | ○ | ○ | ○ | ○ | ○ | ○ | ○ | 6306.0 |
| 3 | Dissolution rate (%) for 30 minutes Test solution: pH 1.2 | ◎ | ○ | ○ | — | — | ○ | — | ◎ | ○ | ○ | — |

Evaluation Results of Test Example 1 (Evaluation of Slipping Property)

In Comparative Example 1 (uncoated tablets A), Comparative Example 2 (uncoated tablets A subjected to common film coating), and Comparative Example 3, in which a carboxyvinyl polymer and xanthan gum were used but polyvalent metal salts were not used, the maximum stress and the area under the stress-distance curve showed great values, and thus, it was assumed that the tablets had a poor slipping property on the mucosa and could be hardly swallowed. In Comparative Example 3, since polyvalent metal ions were not generated by water, the carboxyvinyl polymer was not crosslinked by the polyvalent metal ions. In Examples 1 to 4 and 1-1 to 1-5, in which a carboxyvinyl polymer, polyvalent metal salts and xanthan gum were used, the stress was 41 g or less, the area under the stress-distance curve was 516 g·mm or less. Thus, it was assumed that the tablets could be easily swallowed.

Also, in Examples 6 and 7 in which maltitol or trehalose was used instead of erythritol, in Examples 8 and 9-1 in which guar gum or sodium alginate was used instead of xanthan gum, and in Example 9-2 in which sodium alginate was used instead of a carboxyvinyl polymer, the values of the maximum stress and the area under the stress-distance curve were small, and thus, it was assumed that they could be easily swallowed.

Moreover, the slipping property of Examples 1-P and 2-P was equivalent to that of Examples 1 and 2. From this result, it was confirmed that, even if the compositions of uncoated tablets are different, if the shapes of the uncoated tablets are the same and the coating of the present invention is applied, the same level of slipping property can be obtained.

Furthermore, slight gelation of the coated mini-tablets obtained in Reference Example 2 was observed as a result of addition of water. However, the maximum stress (62.7 g) and the area under the stress-distance curve (786 g·mm) of Reference Example 2 were both greater than those of the Examples of the present invention. Hence, it was assumed that the tablets had a poor slipping property on the mucosa and could be hardly swallowed.

In the studies of Example 5 and the subsequent examples, seal coating was carried out. There was found almost no influence of the seal coating on the measurement values. Considering the results of uncoated tablets as well, it was assumed that the slipping properties of tables having various surface properties can be improved by performing the coating of the present invention on the outermost layers thereof.

As shown in Examples 12, 13, and 15-23, although sucralose was added to a coating solution, a good slipping property could be achieved.

It is to be noted that, in Tables 7 and 8, the open circle in the "maximum stress" column indicates a stress of 41 g or less, and the open circle in the "area under the stress-distance curve" column indicates the value of the area under the stress-distance curve that is 516 g·mm or less.

Evaluation of Test Example 2 (Evaluation of Bitter Taste-Masking)

The concentration of levofloxacin hydrate in the discharged liquid obtained after dropwise addition of water for 2 minutes was significantly higher in both Comparative Example 1 (uncoated tablets A) and Comparative Example 2 (uncoated tablets A subjected to common film coating) than in other examples. The concentration levofloxacin hydrate in Comparative Example 2 was lower than that of Comparative Example 1, but its masking effect was considered to be insufficient. In Examples 1-4 and 1-1 to 1-5 in which a carboxyvinyl polymer, polyvalent metal salts and xanthan gum were used, the concentration of the dissolved solution after dropwise addition of water for 2 minutes was 3 μg/mL or less, and thus, the tablets are considered to have a high bitter taste-masking effect. From these results, it became clear that a combination of a carboxyvinyl polymer with xanthan gum achieves a high bitter taste-masking effect.

Further, in Example 5 and the subsequent examples, the amount of the over-coating solution was decreased for the studies. In these examples, in the case of levofloxacin hydrate, the concentration of the dissolved solution after dropwise addition of water for 30 seconds was found to be 50 µg/mL or less. In Examples 5 to 9-2 and Examples 12 and 13 in which levofloxacin hydrate-containing uncoated tablets C were subjected to over-coating, the concentration of the drug in the discharged solution was low, and it was approximately 1/180 to 1/3 of that of Comparative Example 5 (uncoated tablets C subjected to only seal coating). In Examples 14 to 23 in which any of valaciclovir hydrochloride-containing uncoated tablets D to G was subjected to over-coating, the concentration of the drug in the discharged solution was low, and it was 1/6000 to 1/100 of that of Comparative Example 6 (uncoated tablets D subjected to only seal coating) (for example, the drug concentration in the discharged solution in Example 14 was approximately 1/360 of that of Comparative Example 6). Thus, it was confirmed that each over-coating operation provided a practically sufficient masking effect. Still further, in Examples 12 and 13 and Examples 15 to 23 in which sucralose was added, it was anticipated that the unpleasant taste-masking effect was further improved.

The concentrations of the drugs in the discharged solutions in Comparative Examples 2 and 5, in which uncoated tablets were subjected to only seal coating, were lower than Comparative Examples 1 and 4 (about 1/15 and about 1/20, respectively) that were the uncoated tablets of Comparative Examples 2 and 5 before subjecting to seal coating. From these results, it was supposed that a combination of the over-coating of the present invention with the seal coating of the present invention exhibited the effect of enhancing the unpleasant taste-masking effect upon administration and/or the effect of preventing ingredients contained in a drug core, such as an unpleasant taste ingredient, from moving to an over-coating layer during preservation, so as to prevent the incompatibility between the ingredients of the drug core ingredient and the ingredients of the over-coating layer or attenuation of the masking effect.

In particular, in Example 23 in which the over-coating, middle coating and seal coating of the present invention were performed in combination, the drug concentration in the discharged solution was lower than those of other Examples in which the over-coating of the present invention was combined with the middle coating of the present invention, and as a result, a high unpleasant taste-masking effect was confirmed upon administration.

It is to be noted that, in Table 7, the open circle in the "concentration of liquid discharged for 30 seconds" column indicates a dissolved solution concentration of 50 µg/mL or less, and that in Table 8, the open circle in the "concentration of liquid discharged for 30 seconds" column indicates a dissolved solution concentration of 60 µg/mL or less stress.

Evaluation Results of Test Example 3

The dissolution rate of the drug was extremely high in Comparative Examples 1 and 2. In Examples 1 to 4 in which HPMC and sugar alcohol were used, and in Example 2-1 in which Carbopol was not used, but xanthan gum, HPMC and erythritol were used, the dissolution rate was 80% or more for 30 minutes, and thus, they exhibited an excellent dissolution property. In Example 2-2 in which only Carbopol was used as a thickener, a dissolution rate of 70% or more could be obtained. From the results of Example 1 and Example 1-4, it was found that the content of Carbopol in the film that was 12% did not cause a delay in dissolution, but that if the content reached 16% by mass, dissolution was slightly delayed.

From the results of Examples 5 to 7, it was found that even if erythritol is replaced with maltitol or trehalose, an excellent dissolution property is exhibited in any case.

In Example 5 and the subsequent examples, the amount of the over-coating solution was decreased for the studies. In all cases in Example 5 and the subsequent examples, practically sufficient dissolution rates were exhibited, and neither difference in the compositions of uncoated tablets nor influence by seal coating was found.

It is to be noted that, in Tables 7 and 8, the double circle in the "dissolution rate (%) for 30 minutes" column indicates a dissolution rate for 30 minutes that is 80% or more, and the open circle indicates a dissolution rate for 30 minutes that is 60% or more.

As stated above, in the case of the oral composition of the present invention, the surface layer of a tablet promptly turns into a gel in the presence of a small amount of water or saliva, resulting in good cohesiveness of tablets. Thus, the tablets can easily slip on the mucosa and can be easily swallowed. In addition, the gelated coating film suppresses short-term drug dissolution before it is swallowed, and thus it exhibits an unpleasant taste-masking effect. After it has been swallowed, the film thereof is rapidly disintegrated, so that it does not affect drug efflux.

The invention claimed is:

1. A coating composition comprising:
  a first thickener selected from the group consisting of a carboxyvinyl polymer and sodium alginate;
  a polyvalent metal compound;
  at least one type of a second thickener selected from the group consisting of xanthan gum, guar gum and sodium alginate, with the proviso that when the first thickener is sodium alginate the second thickener is not sodium alginate;
  hydroxypropylmethylcellulose; and
  a sugar or sugar alcohol having a solubility at 20° C. of 30 g or more in 100 ml of water,
  wherein the content of the first thickener is 3% to 20% by mass, and the content of the hydroxypropylmethylcellulose is 5% to 35% by mass, wherein % by mass is based on total mass of all ingredients excluding a solvent, and
  wherein the coating composition is configured for coating at least one drug core selected from the group consisting of a tablet core, a pill core, a capsule core, a pellet core and a granule core.

2. The coating composition according to claim 1, wherein the content of the second thickener is 10% to 40% by mass.

3. The coating composition according to claim 1, wherein the content of the sugar or sugar alcohol is 10% to 50% by mass.

4. The coating composition according to claim 1, wherein the content of the polyvalent metal compound is 2% to 15% by mass based on the content of the first thickener.

5. The coating composition according to claim 1, wherein it comprises alcohol as a solvent.

6. The coating composition according to claim 1, wherein the composition is used for spray-coating.

7. The coating composition according to claim 1, wherein the sugar or sugar alcohol is selected from the group consisting of erythritol, maltitol and trehalose.

8. The coating composition according to claim 1, wherein the mixing ratio between the hydroxypropylmethylcellulose and the sugar or sugar alcohol is 1:1 to 1:4.

9. An oral composition having:
a drug core containing an active ingredient; and
over the drug core,
a coating comprising
   a first thickener selected from the group consisting of a carboxyvinyl polymer and sodium alginate,
   a polyvalent metal compound,
   at least one type of a second thickener selected from the group consisting of xanthan gum, guar gum and sodium alginate, with the proviso that when the first thickener is sodium alginate the second thickener is not sodium alginate,
   hydroxypropylmethylcellulose; and
   a sugar or sugar alcohol having a solubility at 20° C. of 30 g or more in 100 ml of water,
   wherein the content of the first thickener is 3% to 20% by mass, and the content of the hydroxypropylmethylcellulose is 5% to 35% by mass, wherein % by mass is based on total mass of all ingredients in the coating, and
   wherein the drug core is at least one drug core selected from the group consisting of a tablet core, a pill core, a capsule core, a pellet core and a granule core.

10. The oral composition according to claim 9, wherein the content of the second thickener is 10% to 40% by mass.

11. The oral composition according to claim 9, wherein the content of the sugar or sugar alcohol is 10% to 50% by mass.

12. The oral composition according to claim 9, wherein the content of the polyvalent metal compound is 2% to 15% by mass based on the content of the first thickener.

13. The oral composition according to claim 9, wherein the sugar or sugar alcohol is selected from the group consisting of erythritol, maltitol and trehalose.

14. The oral composition according to claim 9, wherein the mixing ratio between the hydroxypropylmethylcellulose and the sugar or sugar alcohol is 1:1 to 1:4.

* * * * *